United States Patent
Cai et al.

(10) Patent No.: US 11,725,239 B2
(45) Date of Patent: Aug. 15, 2023

(54) QUANTITATIVE ANALYSIS OF SINGLE-CELL PROTEINS BY IDENTIFICATION AND QUANTIFICATION SEPARATION (DUET)

(71) Applicant: California Institute of Technology, Pasadena, CA (US)

(72) Inventors: Long Cai, Pasadena, CA (US); Chang Ho Sohn, Seoul (KR); Yandong Zhang, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 110 days.

(21) Appl. No.: 17/103,757

(22) Filed: Nov. 24, 2020

(65) Prior Publication Data

US 2021/0180127 A1 Jun. 17, 2021

Related U.S. Application Data

(60) Provisional application No. 62/940,053, filed on Nov. 25, 2019.

(51) Int. Cl.
*C12Q 1/68* (2018.01)
*C12Q 1/6874* (2018.01)
*C12Q 1/6806* (2018.01)
*C12Q 1/6818* (2018.01)
*C12Q 1/6825* (2018.01)

(52) U.S. Cl.
CPC ......... *C12Q 1/6874* (2013.01); *C12Q 1/6806* (2013.01); *C12Q 1/6818* (2013.01); *C12Q 1/6825* (2013.01)

(58) Field of Classification Search
CPC .. C12Q 1/6874; C12Q 1/6806; C12Q 1/6818; C12Q 1/6825
See application file for complete search history.

(56) References Cited

U.S. PATENT DOCUMENTS

| | | |
|---|---|---|
| 2013/0053544 A1 | 2/2013 | Howarth |
| 2018/0088112 A1 | 3/2018 | Fan et al. |
| 2019/0144854 A1 | 5/2019 | Ismagilov et al. |
| 2020/0131233 A1 | 4/2020 | Howarth et al. |

FOREIGN PATENT DOCUMENTS

| | | |
|---|---|---|
| WO | WO 2018/017949 A1 | 1/2018 |
| WO | WO 2020/206285 A1 | 10/2020 |

OTHER PUBLICATIONS

International Search Report and Written Opinion dated Mar. 23, 2021 for PCT Application No. PCT/US2020/062100, 16 pages.

Rosenberg, et al: "Scaling single cell transcriptomics through split pool barcoding", bioRxiv; Feb. 2, 2017; XP055648510, doi: 10.1101/15163, 14 pages.

Zhang, et al:"Detecting protein and post-translational modifications in single cells with identification and quantification separation (DUET)", Communications Biology; Aug. 3, 2020; vol. 3(1), pp. 1-6; XP055783529.

Breker, et al: "A novel single-cell screening platform reveals proteome plasticity during yeast stress responses", Journal of Cellular Biology 2013; vol. 200(6), pp. 839-850.

Budnik, et al: "SCOPE-MS: mass spectrometry of single mammalian cells quantifies proteome heterogeneity during cell differentiation", Genome Biology; Oct. 22, 2018; vol. 19(1), pp. 161.

Cai, et al: "Frequency-modulated nuclear localization bursts coordinate gene regulation", Nature; Sep. 25, 2008; vol. 455(7212), pp. 485-490.

Chin: "Expanding and reprogramming the genetic code", Nature; Oct. 4, 2017; vol. 550(7674), pp. 53-60.

Cusanovich, et al: "Epigenetics: Multiplex single-cell profiling of chromatin accessibility by combinatorial cellular indexing", Science; May 22, 2015; vol. 348, Issue 6237, pp. 910-914.

Dieterich, et al: "Selective identification of newly synthesized proteins in mammalian cells using biorthogonal noncanonical amino acid tagging (BONCAT)", Proceedings of the National Academy of Sciences; Jun. 20, 2006; vol. 103(25), pp. 9482-9487.

Eriksson, et al: "Regulation of histone gene expression", Genetics; May 2012; vol. 191, pp. 7-20.

Garmendia-Torres, et al: "Multiple inputs ensure yeast cell size homeostasis during cell cycle progression", eLife; Jul. 4, 2018; vol. 7(e34025).

Hughes, et al: "Single-cell western blotting", Nature Methods; Jul. 2014; vol. 11(7), pp. 749-755.

Kang, et al: "Stabilizing Isopeptide bonds revealed in gram-positive bacterial pilus structure", Science; Dec. 7, 2007; vol. 318, Issue 5856, pp. 1625-1628.

Keeble, et al: "Approaching infinite affinity through engineering of peptide-protein interaction", Proceedings of the National Academy of Sciences; Dec. 26, 2019; vol. 116(52), pp. 26523-26533.

Kinoshita, et al: "Separation and detection of large phosphoproteins using Phos-tag SDS-PAGE", Nat. Protocol. 2009; vol. 4(10), pp. 1513-1521.

Kivioja, et al: "Counting absolute numbers of molecules using unique molecular identifiers", Nature Methods; Nov. 20, 2011; vol. 9, pp. 72-74.

Levine, et al: "Functional roles of pulsing in genetic circuits", Science; Dec. 6, 2013; vol. 342(6163), pp. 1193-1200.

(Continued)

*Primary Examiner* — Jezia Riley
(74) *Attorney, Agent, or Firm* — Squire Patton Boggs (US) LLP

(57) ABSTRACT

The present application describes compositions and methods for identifying and quantitating molecular targets within a cellular environment. Specifically, provided herein are compositions and methods for separately identifying and quantifying each of one or more molecular targets from a single cell. More specifically, provided herein are compositions and methods for separately identifying and quantifying the same molecular target from a single cell.

20 Claims, 14 Drawing Sheets

Specification includes a Sequence Listing.

(56) References Cited

OTHER PUBLICATIONS

Marcon, et al: "Assessment of a method to characterize antibody selectivity and specificity for use in immunoprecipitation", Nature Methods; Aug. 2015; vol. 12(8), pp. 725-731.

Ogawa, et al: "Seed metabolome analysis of a transgenic rice line expressing cholera toxin-B subunit", Scientific Reports; Jul. 12, 2017; vol. 7(5196), pp. 1-7.

Rabilloud, et al: "Two-dimensional gel electrophoresis in proteomics: a tutorial", J. Proteomics; Sep. 6, 2011; vol. 74(10); pp. 1829-1841.

Reddington, et al: "Secrets of a covalent interaction for biomaterials and biotechnology: SpyTag and SpyCatcher", Current Opinion in Chemical Biology 2015; vol. 29, pp. 94-99.

Regot, et al: "High-sensitivity measurements of multiple kinase activities in live single cells", Cell; Jun. 19, 2014; vol. 157(7), pp. 1724-1734.

Schulze, et al: "Spliting the task: Upb8 and Ubp10 deubiquitinate different cellular pools of H2BK123", Genes & Development 2011; vol. 25, pp. 2242-2247.

Takemori, et al: "Top-down/bottom-up mass spectrometry workflow using dissolvable polyacrylamide gels", Anal. Chem; Jul. 19, 2017; vol. 89(16), pp. 8244-8250; acs.analchem.7b00357.

Washburn, et al: "Large-scale analysis of the yeast proteome by multidimensional protein identification technology", Nature Biotechnology; Mar. 2001; vol. 19, pp. 242-247.

Zakeri, et al: "Peptide tag forming a rapid covalent bond to a protein, through engineering a bacterial adhesion", Proceedings of the National Academy of Sciences; Mar. 20, 2012; vol. 109(12), pp. E690-E697; epub Feb. 24, 2012.

Zambrano, et al: "NF-kB oscillations translate into functionally related patterns of gene expression", eLife; Jan. 14, 2016; vol. 5(e09100).

After Spycatcher-oligo conjugation   After 1st ligation   After 2nd ligation

Forward PCR handle   Reverse PCR handle
Barcode oligo : TTAACTGCAAGTCAAGCCAT   ACTATCCTACTCAACATCCT
Dummy oligo : CAGCTTCTGTGTCTTATCTC   TAAGGTCTATACGCGGGAAT 2nd ligation dummy oligo:

5'P-ATCCTGTCAT CGGCACTTTAAGGTCTATACGCGGGAAT 
TAMRA dye

Final product:

→ H2Bub-oligo
→ H2B-oligo

→ Spycatcher-oligo (leftover nonspecific binding)

→ leftover 2nd oligo

Ladder   H2B/H2Bub
after 2nd ligation

SEQUENCE LISTING

<160> NUMBER OF SEQ ID NOS: 15

<210> SEQ ID NO 1

```
<211> LENGTH: 13
<212> TYPE: PRT
<213> ORGANISM: artificial
<220> FEATURE:
<223> OTHER INFORMATION: Spytag

<400> SEQUENCE: 1

Ala His Ile Val Met Val Asp Ala Tyr Lys Pro Thr Lys
1               5                   10

<210> SEQ ID NO 2
<211> LENGTH: 139
<212> TYPE: PRT
<213> ORGANISM: Artificial Sequence
<220> FEATURE:
<223> OTHER INFORMATION: Spycatcher1

<400> SEQUENCE: 2

Met Ser Tyr Tyr His His His His His His Asp Tyr Asp Ile Pro Thr
1               5                   10                  15

Thr Glu Asn Leu Tyr Phe Gln Gly Ala Met Val Asp Thr Leu Ser Gly
            20                  25                  30

Leu Ser Ser Glu Gln Gly Gln Ser Gly Asp Met Thr Ile Glu Glu Asp
        35                  40                  45

Ser Ala Thr His Ile Lys Phe Ser Lys Arg Asp Glu Asp Gly Lys Glu
    50                  55                  60

Leu Ala Gly Ala Thr Met Glu Leu Arg Asp Ser Ser Gly Lys Thr Ile
65                  70                  75                  80

Ser Thr Trp Ile Ser Asp Gly Gln Val Lys Asp Phe Tyr Leu Tyr Pro
                85                  90                  95

Gly Lys Tyr Thr Phe Val Glu Thr Ala Ala Pro Asp Gly Tyr Glu Val
            100                 105                 110

Ala Thr Ala Ile Thr Phe Thr Val Asn Glu Gln Gly Gln Val Thr Val
        115                 120                 125

Asn Gly Lys Ala Thr Lys Gly Asp Ala His Ile
    130                 135

<210> SEQ ID NO 3
<211> LENGTH: 20
<212> TYPE: DNA
<213> ORGANISM: artificial
<220> FEATURE:
<223> OTHER INFORMATION: Forward PCR Handle

<400> SEQUENCE: 3
ttaactgcaa gtcaagccat                                           20

<210> SEQ ID NO 4
<211> LENGTH: 18
<212> TYPE: DNA
<213> ORGANISM: artificial
<220> FEATURE:
<223> OTHER INFORMATION: UMI
<220> FEATURE:
<221> NAME/KEY: misc_feature
<222> LOCATION: (8)..(18)
<223> OTHER INFORMATION: n is a, c, g, or t

<400> SEQUENCE: 4
cgaattcnnn nnnnnnnn                                             18

<210> SEQ ID NO 5
<211> LENGTH: 18
```

```
<212> TYPE: DNA
<213> ORGANISM: artificial
<220> FEATURE:
<223> OTHER INFORMATION: First cell barcode

<400> SEQUENCE: 5
ctatgatcct gagactta                                                  18

<210> SEQ ID NO 6
<211> LENGTH: 18
<212> TYPE: DNA
<213> ORGANISM: artificial
<220> FEATURE:
<223> OTHER INFORMATION: Second cell barcode

<400> SEQUENCE: 6
atcctgtcat tctctaga                                                  18

<210> SEQ ID NO 7
<211> LENGTH: 20
<212> TYPE: DNA
<213> ORGANISM: artificial
<220> FEATURE:
<223> OTHER INFORMATION: Reverse PCR Handle

<400> SEQUENCE: 7
actatcctac tcaccatcct                                                20

<210> SEQ ID NO 8
<211> LENGTH: 19
<212> TYPE: DNA
<213> ORGANISM: artificial
<220> FEATURE:
<223> OTHER INFORMATION: Second T7 ligation bridge

<400> SEQUENCE: 8
atgacaggat taagtctag                                                 19

<210> SEQ ID NO 9
<211> LENGTH: 20
<212> TYPE: DNA
<213> ORGANISM: artificial
<220> FEATURE:
<223> OTHER INFORMATION: First T7 ligation bridge

<400> SEQUENCE: 9
gaattcgatg gcttgacttg                                                20

<210> SEQ ID NO 10
<211> LENGTH: 20
<212> TYPE: DNA
<213> ORGANISM: artificial
<220> FEATURE:
<223> OTHER INFORMATION: Dummy oligo

<400> SEQUENCE: 10
taagggcgca tatctggaat                                                20

<210> SEQ ID NO 11
<211> LENGTH: 38
<212> TYPE: DNA
<213> ORGANISM: artificial
<220> FEATURE:
<223> OTHER INFORMATION: 2nd Ligation Dummy oligo

<400> SEQUENCE: 11
```

```
atcctgtcat cggcacttta aggtctatac gcgggaat                              38
```

```
<210> SEQ ID NO 12
<211> LENGTH: 16
<212> TYPE: DNA
<213> ORGANISM: artificial
<220> FEATURE:
<223> OTHER INFORMATION: Cell barcode

<400> SEQUENCE: 12
ttaccgactt accgac                                                      16

<210> SEQ ID NO 13
<211> LENGTH: 16
<212> TYPE: DNA
<213> ORGANISM: artificial
<220> FEATURE:
<223> OTHER INFORMATION: Cell barcode

<400> SEQUENCE: 13
ttaccgacgt acacct                                                      16

<210> SEQ ID NO 14
<211> LENGTH: 16
<212> TYPE: DNA
<213> ORGANISM: artificial
<220> FEATURE:
<223> OTHER INFORMATION: Cell barcode

<400> SEQUENCE: 14
ttaccgactc gtctga                                                      16

<210> SEQ ID NO 15
<211> LENGTH: 20
<212> TYPE: DNA
<213> ORGANISM: artificial
<220> FEATURE:
<223> OTHER INFORMATION: Cell barcode

<400> SEQUENCE: 15
ctctattctg tgtcttcgac                                                  20
```

QUANTITATIVE ANALYSIS OF SINGLE-CELL PROTEINS BY IDENTIFICATION AND QUANTIFICATION SEPARATION (DUET)

CROSS-REFERENCE TO RELATED APPLICATIONS

The present application claims the benefit of U.S. provisional application No. 62/940,053, filed Nov. 25, 2019, the content of which is hereby incorporated by reference in its entirety.

STATEMENT REGARDING FEDERALLY-SPONSORED RESEARCH

This invention was made with government support under Grant No. HL145609 awarded by the National Institutes of Health. The government has certain rights in the invention.

REFERENCE TO SEQUENCE LISTING SUBMITTED VIA EFS-WEB

This application includes an electronically submitted sequence listing in .txt format. The .txt file contains a sequence listing entitled "439915 00066 SEQ LIST_ST25.txt" created on Mar. 4, 2021 and is 5000 bytes in size. The sequence listing contained in this .txt file is part of the specification and is hereby incorporated by reference herein in its entirety.

FIELD

Provided herein are compositions and methods for identifying and quantitating molecular targets within a cellular environment. Specifically, provided herein are compositions and methods for separately identifying and quantifying each of one or more molecular targets from a single cell. More specifically, provided herein are compositions and methods for separately identifying and quantifying the same molecular target from a single cell.

BACKGROUND

Analysis of a molecular target from a single cell has proven challenging. This has been due at least in part to the minute quantities of the molecular targets from single cells.

Locating and quantitating molecular targets in a cell can be crucial for understanding the functions of such molecules. For example, transcription profiling of cells is essential for many purposes. Microscopy imaging, which can resolve multiple mRNAs in single cells, can provide valuable information regarding transcript abundance and localization, which are important for understanding the molecular basis of cell identify and developing treatment for diseases. Protein post-translational modification (PTM) states of proteins are often involved in dynamic and oscillatory processes that are not synchronized in a population and show substantial single-cell heterogeneities. Cai et al., 2008, *Nature* 455; Regot et al., 2014, *Cell* 157, 1724-1734. Zambrano et al., 2016, *Elife* 5, e09100; Levine et al., 2013, *Science* 342, 1193-1200 (2013).

Single cell analysis with conventional techniques faces several main challenges. First, single cells typically do not provide enough material (RNA, DNA, protein, sugar, or lipids) for analysis. There are approximately 1-2 copies of each DNA, 1-1000 copies of each mRNA, and on average 1000 copies of each protein species in a given cell. Unlike DNA and RNA, protein and other species cannot be amplified with current techniques.

Indeed, conventional protein detection methods, such as Western blots, enzyme-linked immunosorbent assay (ELISA) and mass spectrometry are difficult to downscale to the single-cell level. Hughes et al., 2014, *Nat. Methods* 11, 749-755. Furthermore, antibody-based methods rely on the availability of good affinity reagents which are often the limiting factor in experiments. Marcon et al., 2015, *Nat. Methods* 12, 725-731. Recently, great advances have been made in single-cell mass spectrometry analysis using reporter ions and cell pooling with great potential for further increases in sensitivity, throughput, and coverage. Budnik et al., 2018, *Genome Biol.* 19, 161. Conventional techniques such as mass spectrometry have attempted to attack this problem by improving the sensitivity of instrumentation.

However, conventional separation and analysis methods often introduce biases in the sample by enriching for certain molecular species while diluting others. This can distort the relative abundances of the components in the cell. For example, ionization in mass spec significantly biases for charged and volatile species. In many cases, the full functional diversity of the molecule, such as phosphorylation, ubiquitination, and other covalent modification, cannot be explored by labeling methods or antibodies or other affinity based methods.

What are needed is the art are better compositions and methods for identifying and quantifying molecular targets from a single cell.

SUMMARY

Provided herein are compositions and methods for identifying and quantifying target molecules from single cells, down to as few as a single molecule from a single cell. The methods and compositions are based, at least in part, on separating the identification and quantification parts of the analysis into distinct steps. Identification proceeds by techniques such as electrophoresis, mass spectrometry, or other techniques. Quantification proceeds by decoding a label, for instance by decoding an oligonucleotide label by sequencing. In doing so, the major challenges of single cell analysis can be resolved. In certain embodiments, the compositions and methods allow highly multiplexed and quantitative analysis of molecular species in single cells using conventional biochemical separation techniques and conventional sequencing techniques.

In one aspect, provided herein are methods for identifying one or more macromolecules in a plurality of cells with up to single cell resolution. The methods comprise several steps. In one step, the one or more macromolecules are labeled in situ, for instance in cells. Each label identifies one cell of the plurality of cells. Useful labels and techniques for labeling are described herein. In a further step, the plurality of cells, comprising the labeled one or more macromolecules is pooled. Pooling the cells can provide a sufficient amount of each macromolecule to facilitate identification of the macromolecule. In a further step, the one or more labeled macromolecules are separated from the pooled cells. In a further step, the labeled macromolecules are analyzed separately for identity and quantity. In certain embodiments, the labels are removed from the macromolecules. In certain embodiments, the macromolecules are identified. Identification can proceed according to standard techniques, such as electrophoresis, mass spectrometry, and other macromolecular identification techniques. In certain embodiments, the labels are decoded. Decoding can proceed with standard techniques. In certain embodiments, decoding is by oligonucleotide sequencing. From the decoding, a macromolecule with a particular label code can be associated with the cell from which it originated, thereby identifying the macromolecule in the cell.

In another aspect, provided herein are methods for identifying and quantifying one or more macromolecules in a plurality of cells with up to single cell resolution. The methods comprise several steps. In one step, the one or more macromolecules are labeled. Each label identifies one cell of the plurality of cells. Useful labels and techniques for labeling are described herein. In a further step, the plurality of cells, comprising the labeled one or more macromolecules is pooled. Pooling the cells can provide a sufficient amount of each macromolecule to facilitate identification of the macromolecule. In a further step, the one or more labeled macromolecules are separated from the pooled cells. In a further step, the labeled macromolecules are analyzed separately for identity. In certain embodiments, the labels are removed from the macromolecules. In certain embodiments, the macromolecules are identified. Identification can proceed according to standard techniques, such as electrophoresis, mass spectrometry, and other macromolecular identification techniques. In certain embodiments, the labels are decoded. Decoding can proceed with standard techniques. In certain embodiments, decoding is by oligonucleotide sequencing. From the decoding, each macromolecule with a particular label code can be associated with the cell from which it originated. In certain embodiments, the number of copies of an identified macromolecule with a particular label indicates the quantity of copies of that macromolecule in a single cell. In particular embodiments, the number of copies of an identified macromolecule with a particular label correlates to the quantity of copies of that macromolecule in a single cell In certain embodiments, the methods and compositions provide herein can overcome the limitations of conventional approaches. As the cellular origins of macromolecules are preserved in the labels, for instance barcode oligonucleotides, macromolecules can be pooled from thousands to millions of cells to provide sufficient material for identification, for instance by a gel or column chromatography or mass spectrometry. Their cellular identity can be decoded separately by decoding the label, for instance by sequencing. The number of reads of a label, for instance a barcode oligonucleotide, can indicate quantity of the macromolecule in the cell, for instance by correlation.

In certain embodiments, provided herein are compositions useful in the methods. In certain embodiments, the compositions comprise a plurality of cells wherein one or more of the cells comprise one or more macromolecules, each labeled with a label that identifies each cell relative to the other cells in the plurality. In certain embodiments, provided herein are macromolecules, wherein each macromolecule comprises a spytag. In certain embodiments, the spytag is covalently linked to the rest of the macromolecule. In certain embodiments, the spytag is further linked to a spycatcher protein. In certain embodiments, the spycatcher protein is further linked to a label. In certain embodiments, the label comprises an oligonucleotide, for instance a barcode oligonucleotide. Particular labeled macromolecules, and methods for their preparation, are described herein. In further embodiments, provided herein are labels comprising a spycatcher protein covalently linked to a reactive group, capable of reacting with a tagged molecular target, and further covalently linked to an oligonucleotide.

The methods and compositions are useful for identifying and quantifying macromolecules from single cells. As demonstrated in the examples herein, the methods and compositions were used to quantify post-translational modification isoforms of a protein in single cells with high detection efficiency (~40%) using bulk separation methods.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Those of skill in the art will understand that the drawings, described below, are for illustrative purposes only. The drawings are not intended to limit the scope of the present teachings in any way.

FIG. 1a. The cells are uniquely barcoded, pooled together, lysed, and analyzed by gel electrophoresis to identify different protein and post-translational modifications. After protein identification, the protein-oligo complexes are recovered and the oligo part is PCR amplified to generate a sequencing library. The single-cell protein abundance can be quantified from cell barcodes and unique UMIs from next-generation sequencing. FIG. 1b. S. cerevisiae strain containing spytag at the C-terminal of targeted protein is constructed and the cells are reacted with spycatcher-oligo to covalently attach DNA oligo to targeted proteins in situ. Then the cells are combinatorially indexed with two rounds of "split-pool" barcoding. The cells are firstly distributed into a 96-well plate, and well-specific barcodes were ligated to the DNA oligo on the proteins via T7 ligation. Then the cells were pooled together and randomly distributed again into another 96-well plate where second barcodes were ligated. FIG. 1c. The oligo design. The oligo used for synthesizing spycatcher-DNA oligo conjugate is 20nt (SEQ ID NO:3), which was also used as a PCR handle in sequencing library generation. The 5'-phosphorylated 1st ligation barcode oligo contains a T7 site (7nt, for 1st round T7 ligation), a UMI sequence (12nt) (SEQ ID NO:4), a cell barcode (8nt) (SEQ ID NO:5), and another T7 site (10nt, for 2nd round T7 ligation). The 5'-phosphorylated 2nd ligation barcode oligo (SEQ ID NOS:6-7) contains a T7 site (10nt, for 2nd round T7 ligation), a cell barcode (8nt) and the reverse PCR handle (20nt). The ligation bridge sequences (SEQ ID NOS:8-9) are complementary to T7 sites. FIG. 1d. Western blot analysis of different target proteins (SNF1, PRE1, GLC7, and H2B) after-oligo spycatcher reaction, after the first ligation and after the second ligation. For H2B protein, H2B (lower band) and its monoubiquitination isoform H2Bub (upper band) are separated since they have different molecular weights.

FIG. 2a. Cell barcode identification from sequencing results. The number of reads per cell barcode was plotted in descending order. A clear cutoff (dashed line) could be identified to separate real barcodes (with a high number of reads) from a large number of spurious cell barcodes (with a low number of reads). The inset shows accumulated reads percentage. The gray area corresponds to real cell barcodes, which account for 97.3% of the total filtered reads. FIG. 2b. Histogram of H2B copy number in single cells. FIG. 2c. H2B and H2Bub copy number in single cells, each dot corresponding to one single cell. FIG. 2d. The H2Bub/H2B ratio in single cells. Each dot represents a single cell. The red dashed line indicates the population-average H2Bub/H2B ratio. The gray line divides the cells into G1 and G2/M cell-cycle stages according to the H2B copy number. The green box indicates more ubiquitinated populations in the G1 stage. FIG. 2e. The distributions of H2Bub/H2B ratio for cells in G1 and G2/M stages, respectively. The two stages have different distributions with Welch's t-test. FIG. 2f. Western blot images of H2B for the wild-type strain (WT) and the UBP8 and UBP10 double knockout strain (DKO). The H2Bub/H2B ratios measured from the image are ~12% in WT and ~69% in DKO respectively. FIG. 2g. The H2Bub/H2B ratios as a function of H2B copy number in single cells for DKO strain. Each dot represents a single cell. The red dashed line is the population-average H2Bub/H2B ratio. The green box indicates hyper-ubiquitinated populations in the G1 stage.

FIG. 3a. Strategy for spycatcher-oligo conjugate synthesis. Spycatcher with a cysteine at the C-terminal region was reacted with the maleimide-PEG4-tetrazine to generate spycatcher-tetrazine. 5' amine-modified oligo was reacted with NHS ester-PEG4-TCO to generate oligo-TCO. The spycatcher-tetrazine and oligo-TCO were then conjugated together via click chemistry. FIG. 3b. The gel electrophoresis results for spycatcher-oligo (20mer) purification using ion-exchange chromatography. The numbers are the different fractions from ion-exchange chromatography. Spycatcher-DNA oligo conjugate (spycatcher-20mer) is separated from the leftover spycatcher.

FIG. 4a. The H2B and H2Bub bands shift up, indicating a successful reaction. FIG. 4b. The intensities of the regions (yellow boxes in a)) were determined from images after removing the background. The intensity for the leftover signal is less than 10% of the product, showing that the reaction efficiency is about 90%.

FIG. 6a. The dummy oligo (SEQ ID NOS:10 and 15) has the same length as the barcode oligo, but has different sequences in the PCR handle (SEQ ID NO:3 and 7). Therefore, proteins labeled with dummy oligo will co-migrate with proteins labeled with barcode oligo during gel electrophoresis, but will not be amplified during library preparation. FIG. 6b. A TAMRA dye is incorporated into the second ligation oligo (SEQ ID NO:11) used in the dummy sample. The protein-oligo conjugate can then be visualized on the gel using fluorescence. FIG. 6c. The fluorescent gel image using a typhoon scanner. H2Bub-oligo and H2B-oligo conjugated with TAMRA dye can be identified. Leftover 2nd ligation oligo can also be identified. We also observed a band whose size corresponds to spycatcher-oligo after two rounds of barcodes ligation. This may come from unreacted, non-specific binding spycatcher-oligos inside the cells that are further barcoded during pool-split barcoding. This spycatcher-full-length oligo product will interfere with quantification if not separated by gel electrophoresis.

FIG. 7a. Two bands corresponding to targeted proteins (H2Bub, H2B) and a band corresponding to background were cut from the gel and DNA-protein conjugates were extracted and sequenced by next-generation sequencing. FIG. 7b. The total number of reads per barcode was plotted in descending order for the H2Bub band (FIG. 2b). Similar to the H2B band, a clear cut-off can be identified that separates real cell barcodes from spurious barcodes with a low number of reads. The real cell barcodes identified from H2B and from H2Bub are almost the same (848 out of 850), further confirming that those barcodes represent real single cells. FIG. 7c. By contrast, barcodes from the background do not show a clear cutoff. FIG. 7d. The unique UMIs (aka, protein copy numbers) associated with the real barcodes from H2Bub and H2B bands and from the background band. This result shows that protein is clearly resolved during electrophoresis and the gel has a low background.

FIG. 8a. The number of reads for each UMI in 3 example cells. The number of reads associated with UMIs varies from 16 to 1, demonstrating the necessity of using UMI to correct PCR duplication. The inset shows the total reads and unique UMIs associated with each barcode (SEQ ID NOS:12-14). FIG. 8b. The number of unique UMI identified when sublength of UMIs is taken for 3 example cells. The number of UMIs increased with the length of the UMIs and reached a plateau after around 10nt, indicating that the length of UMI (12nt) have enough coding space to encode all proteins in single cells. FIG. 8c. The number of unique UMIs identified when sequencing depth (the number of total reads) is subsampled. As sequencing depth increases, the number of uniquely identified UMIs increases and reached a plateau at full sequencing depth (1.0), indicating that all the UMIs are sufficiently sampled. Based on these premises, the protein copy number from single cells can be presented by the number of unique UMIs.

DETAILED DESCRIPTION OF CERTAIN EMBODIMENTS

Figure 1A:
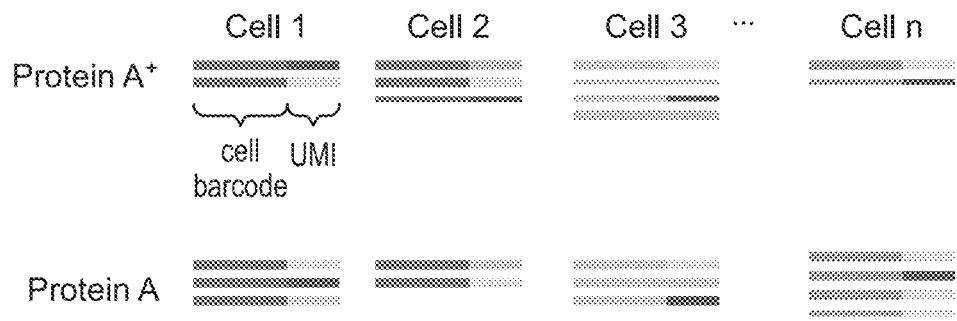
FIGS. 1a-1d. Schematics of iDentification and qUantification sEparaTion (DUET).

Provided herein are compositions and methods for identifying and quantitating molecular targets within a cellular environment. The compositions and methods are useful, for instance, to detect molecular targets from a single cell.

Definitions

Unless otherwise noted, terms are to be understood according to conventional usage by those of ordinary skill in the relevant art.

As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value).

The term "oligonucleotide" refers to a polymer or oligomer of nucleotide monomers, containing any combination of nucleobases, modified nucleobases, sugars, modified sugars, phosphate bridges, or modified bridges.

Oligonucleotides can be of various lengths. In particular embodiments, oligonucleotides can range from about 2 to about 200 nucleotides in length. In various related embodiments, oligonucleotides, single-stranded, double-stranded, and triple-stranded, can range in length from about 4 to about 10 nucleotides, from about 10 to about 50 nucleotides, from about 20 to about 50 nucleotides, from about 15 to about 30 nucleotides, from about 20 to about 30 nucleotides in length. In some embodiments, the oligonucleotide is from about 9 to about 39 nucleotides in length. In some embodiments, the oligonucleotide is at least 4 nucleotides in length. In some embodiments, the oligonucleotide is at least 5 nucleotides in length. In some embodiments, the oligonucleotide is at least 6 nucleotides in length. In some embodiments, the oligonucleotide is at least 7 nucleotides in length. In some embodiments, the oligonucleotide is at least 8 nucleotides in length. In some embodiments, the oligonucleotide is at least 9 nucleotides in length. In some embodiments, the oligonucleotide is at least 10 nucleotides in length. In some embodiments, the oligonucleotide is at least 11 nucleotides in length. In some embodiments, the oligonucleotide is at least 12 nucleotides in length. In some embodiments, the oligonucleotide is at least 15 nucleotides in length. In some embodiments, the oligonucleotide is at least 20 nucleotides in length. In some embodiments, the oligonucleotide is at least 25 nucleotides in length. In some embodiments, the oligonucleotide is at least 30 nucleotides in length. In some embodiments, the oligonucleotide is a duplex of complementary strands of at least 18 nucleotides in length. In some embodiments, the oligonucleotide is a duplex of complementary strands of at least 21 nucleotides in length.

Probe: As used herein, the term "probe" or "probes" refers to any molecules, synthetic or naturally occurring, that can attach themselves directly or indirectly to a molecular target (e.g., an mRNA sample, DNA molecules, protein molecules, RNA and DNA isoform molecules, single nucleotide polymorphism molecules, and etc.). For example, a probe can include a nucleic acid molecule, an oligonucleotide, a protein (e.g., an antibody or an antigen binding sequence), or combinations thereof. For example, a protein probe may be connected with one or more nucleic acid molecules to for a probe that is a chimera. As disclosed herein, in some embodiments, a probe itself can produce a detectable signal. In some embodiments, a probe is connected, directly or indirectly via an intermediate molecule, with a signal moiety (e.g., a dye or fluorophore) that can produce a detectable signal.

As used herein, the term "sample" refers to a biological sample obtained or derived from a source of interest, as described herein. In some embodiments, a source of interest comprises an organism, such as an animal or human. In some embodiments, a biological sample comprises biological tissue or fluid. In some embodiments, a biological sample is or comprises bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and/or chemical phenomena.

As disclosed herein, the term "label" generally refers to a molecule that can recognize and bind to specific target sites within a molecular target in a cell. For example, a label can comprise an oligonucleotide that can bind to a molecular target in a cell. The oligonucleotide can be linked to a moiety that has affinity for the molecular target. The oligonucleotide can be linked to a first moiety that is capable of covalently linking to the molecular target. In certain embodiments, the molecular target comprises a second moiety capable of forming the covalent linkage with the label. In particular embodiments, a label comprises a nucleic acid sequence that is capable of providing identification of the cell which comprises or comprised the molecular target. In certain embodiments, a plurality of cells is labeled, wherein each cell of the plurality has a unique label relative to the other labeled cells.

As disclosed herein, the term "barcode" generally refers to a nucleotide sequence of a label produced by methods described herein. The barcode sequence typically is of a sufficient length and uniqueness to identify a single cell that comprises a molecular target.

Methods

Provided herein are compositions and methods for identifying and quantitating molecular targets within a cellular environment. The compositions and methods are capable of separately identifying and quantifying one or more molecular targets from a single cell. In certain embodiments, the compositions and methods are capable of separately identifying and quantifying the number of copies of the same molecular target from a single cell.

The compositions and methods are based, at least in part, on the discovery that the tasks in conventional analyses can be separated. By separating the tasks, molecular targets can be pooled sufficiently for identification. At the same time, labels from the molecular targets can be decoded sensitively in finite amounts to assign, for instance, the cellular origin of the molecular targets. By separating the tasks, the compositions and methods provided herein provide single-cell sensitivity while avoiding the biases of conventional techniques.

This separation of tasks is accomplished by the following. A target molecule of interest is labeled with a label. The target molecule can be any target molecule deemed suitable to the practitioner of skill. In certain embodiments, the target molecule is a macromolecule. In certain embodiments, the target molecule is a cellular macromolecule. In certain embodiments, the target molecule is a nucleic acid, protein, sugar, or lipid. In certain embodiments, the target molecule is a protein. Proteins include those expressed in cells with or without post-translational modifications.

In certain embodiments, the target molecule is tagged. The tag can be any tag deemed suitable by the person of skill in the art. In certain embodiments, the tag facilitates binding or linking to a label. In certain embodiments, the tag is a member of a binding pair. Useful binding pairs include antibodies and antigens, avidin and biotin, lectins and sugars, and any other binding pair deemed useful to the person of skill. In certain embodiments, the tag is a protein tag, for instance a polyhistidine tag or a FLAG tag. In certain embodiments, the tag is a spytag. In certain embodiments, the tag is a member of a reactive pair. Useful reactive pairs include click chemistry reactive pairs, such as azides and alkynes, nitrones and alkynes, alkenes for instance strained alkenes and azides, alkenes and tetrazines, and alkenes and tetrazoles.

In certain embodiments, the macromolecule is a protein comprising one or more non-natural amino acids. In certain embodiments, the non-natural amino acid is selected from the group consisting of modified cysteine, modified lysine, a modified amino terminal amino acid, modified glutamine, azidohomoalanine, and homopropargylglycine. Cysteine amino acids can be modified with maleimide-based tags. Lysine amino acids and amino termini can be modified with N-hydroxysuccinimide-based tags. Glutamine amino acids can be modified with transglutaminase. Azidohomoalanine (Sigma) and homopropargylglycine (Sigma) provide azide residues capable of click reactions with alkynes for tagging.

In certain embodiments, the macromolecule is a protein, and the tag is a small molecule that binds the protein covalently or non-covalently. The small molecule can be a reversible or an irreversible inhibitor of the protein. In certain embodiments, the small molecule is an inhibitor of a class of enzymes, thereby providing for tagging the class. Useful inhibitors include kinase inhibitors, phosphatase inhibitors, adenosine triphosphate analogs, receptor inhibitors, protease inhibitors, and other inhibitors known to the person of skill.

In certain embodiments, the pair is a spytag-spycatcher pair as described in Kang et al. 2007, Science 318:1625-1628; Zakeri et al., 2012, *Proceedings of the National Academy of Sciences* 109; Keeble, 2019, Proc. Natl. Acad. Sci. USA 116:26523-26533; US 2013/0053544 A1; and US 2020/0131233 A1, the contents of which are hereby incorporated by reference in their entireties. The spytag/spycatcher system provides a pair of reactive recombinant proteins having the capacity for irreversible conjugation, forming an isopeptide bond. Said conjugation can occur spontaneously under a range of pH values (5-8), temperatures(4-37°), buffers and in the presence of nonionic detergents. Reddington and Howarth, *Current Opinion in Chem Biol.*, (2015) 29:94-99. In certain embodiments, the spytag has the amino acid sequence AHIVMVDAYKPTK (SEQ ID NO:1). In certain embodiments, the spytag has an amino acid sequence 80%, 85%, 90%, or 95% identical to SEQ ID NO:1. Sequence identity is determined by standard techniques, for instance BLASTP with standard settings.

The tag can be added to the molecular target by any technique deemed suitable by the person of skill. In certain embodiments, the molecular target is chemically modified with the tag. Useful reactions include modification of cysteine side chains, lysine side chains, and amino-termini with tags bearing appropriate reactive groups. Modification can proceed in cells, for instance in immobilized and lysed cells. In certain embodiments, the molecular target is expressed with a fused tag. These are particularly useful for protein molecular targets. In certain embodiments, a spytag is expressed in the cell fused to the molecular target.

The label can be any label that can be decoded following labeling and separation. In particular embodiments, the label comprises an oligonucleotide. The oligonucleotide comprises a sequence that can be decoded to identify the labeled molecular target. In particular embodiments, the label identifies one or more cells that comprise one or more target molecules. This can be accomplished with any label structure deemed suitable by the practitioner of skill. In particular embodiments, an oligonucleotide sequence of the label identifies a cell out of a plurality of cells. When a sequence can uniquely labels a single cell, the compositions and methods provided herein provide for single-cell analysis of target molecules.

In certain embodiments, the label comprises a moiety capable of binding or linking to a corresponding moiety on the target macromolecule. Useful moiety pairs are described above. In certain embodiments, the label comprises a member of a binding pair. Useful binding pairs include antibodies and antigens, avidin and biotin, lectins and sugars, and any other binding pair deemed useful to the person of skill. In certain embodiments, the label comprises a member of a reactive pair. Useful reactive pairs include click chemistry reactive pairs, such as azides and alkynes, nitrones and alkynes, alkenes for instance strained alkenes and azides, alkenes and tetrazines, and alkenes and tetrazoles. In certain embodiments, the pair is a spytag-spycatcher pair. In particular embodiments the label comprises a spycatcher protein. Useful spycatcher proteins are described in Kang et al. 2007, Science 318:1625-1628; Zakeri et al., 2012, *Proc. Natl. Acad. Sci. USA* 109(12):E690-E697; Keeble, 2019, *Proc. Natl. Acad. Sci. USA* 116:26523-26533; US 2013/0053544 A1; and US 2020/0131233 A1, the contents of which are hereby incorporated by reference in their entireties. In certain embodiments, the spycatcher protein is according to Genbank locus JQ478411.1 or Zakeri et al., 2012, *Proc. Natl. Acad. Sci. USA* 109(12):E690-E697. In certain embodiments, the spycatcher protein has the amino acid sequence of GenBank locus AFD50637.1 (SEQ ID NO:2). In certain embodiments, the spycatcher has an amino acid sequence 80%, 85%, 90%, or 95% identical to SEQ ID NO:2. Sequence identity is determined by standard techniques, for instance BLASTP with standard settings.

In certain embodiments, tagged molecular target is contacted with a label comprising a complementary reactive group (to the tag) linked to an oligonucleotide under conditions sufficient for the tagged protein to bind and form a covalent or non-covalent bond to the label. In certain embodiments, the bond is formed by click chemistry. In certain embodiments, the bond is formed by antibody-antigen binding. In certain embodiments, the bond is formed by avidin-biotin binding. In certain embodiments, the bond is formed by spycatcher-spytag interaction.

In certain embodiments, the oligonucleotide is subjected to one or more rounds of combinatorial ligation. In each round, a new oligonucleotide is ligated to the label oligonucleotide to successively build up the barcode. In certain embodiments, there is one round of combinatorial ligation. In certain embodiments, there are two rounds of combinatorial ligation. In certain embodiments, there are three rounds of combinatorial ligation. In certain embodiments, there are four rounds of combinatorial ligation. In certain embodiments, there are five rounds of combinatorial ligation. In certain embodiments, there are more than five rounds of combinatorial ligation. Each round of combinatorial ligation increases the diversity of oligonucleotide sequences, thereby increasing the number of cells that can be uniquely barcoded. The oligonucleotide should have a sufficient length for the diversity needed for the method. In certain embodiments, the oligonucleotide has a length of about 20 bp, about 30 bp, about 40 bp, about 50 bp, about 60 bp, about 80 bp, about 100 bp, about 150 bp, about 200 bp, about 250 bp, about 300 bp, about 350 bp, about 400 bp, about 450 bp, about 500 bp, 600 bp, about 700 bp, about 800 bp, about 900 bp, or about 1,000 bp.

In certain embodiments, the label further comprises additional moieties to facilitate analysis. In certain embodiments, the label comprises polymerase chain reaction handles that enable amplification of oligonucleotide sequences. In certain embodiments, the oligonucleotides comprise unique molecular identifiers. In certain embodiments, the unique molecular identifiers are random nucleotide sequences that facilitate uniquely identifying a cell of origin.

In certain embodiments, each cell in a plurality of cells is labeled with a unique barcode. This can be accomplished by any technique deemed suitable by the person of skill. In certain embodiments, single cells are isolated and labeled. In advantageous embodiments, unique labeling can be accomplished with serial dilutions followed by labeling reactions. In certain embodiments, unique labeling can be accomplished with split ligation, for instance pool-split ligation such described in FIG. 1 and Cusanovich, et al., 2015 *Science* 348, 910-914, the contents of which are hereby incorporated by reference in their entirety. In certain embodiments, cells are split into several groups. A separate oligonucleotide is ligated to the labels in the cells in each group. Within one group, the oligonucleotides share the same sequence. From group to group, the oligonucleotides differ in sequence. Then, the cells are pooled and split again into several groups. A separate oligonucleotide is ligated to the labels in the cells in each group. Within one group, the oligonucleotides share the same sequence. From group to group, the oligonucleotides differ in sequence. This process is repeated until there is sufficient diversity of label sequences to uniquely identify single cells in the pool. The number of repeats is determined by the number of cells and can be calculated by the person of skill. Cusanovich, et al., 2015 *Science* 348, 910-914.

In the methods, labeled cells are then pooled. Pooling provides a sufficient mass of molecular targets to facilitate identification techniques. Since each cell is uniquely labeled, the contents of a number of cells can be pooled without losing cellular origin information. In the methods, the cells are lysed. Lysing can proceed according to standard techniques. In certain embodiments, pooling precedes lysing. In certain embodiments, lysing precedes pooling. In certain embodiments, pooling and lysing proceed in the same step.

The samples are then analyzed. In certain embodiments, the molecular targets are identified. Advantageously, conventional identification techniques can be used. In certain embodiments, molecular targets are identified by chromatography, high performance liquid chromatography. In certain embodiments, molecular targets are identified by gel chromatography, for instance electrophoresis. Useful techniques include SDS-PAGE, two-dimensional gel electrophoresis, and phosphorylation sensitive gel electrophoresis. In certain embodiments, molecular targets are identified by column chromatography. Useful techniques for further identification include Western blotting, Edman sequencing, and other techniques deemed suitable by the practitioner of skill. In certain embodiments, molecular targets are identified by spectrometry. In certain embodiments, molecular targets are measured by mass spectrometry. Useful techniques include MALDI mass spectrometry.

Analysis also proceeds by decoding the labels. In certain embodiments, labels are cleaved from the target molecules. In certain embodiments, labels are cleaved from the target molecules prior to identification above. In certain embodiments, labels are decoded by sequencing. Sequencing proceeds according to standard techniques, for instance by next generation sequencing. In certain embodiments, label oligonucleotides are amplified, for instance by polymerase chain reaction to facilitate sequencing.

Once a target molecule is identified and its label decoded, its cellular origin can be determined. Each target molecule with a different label originated from a different cell. Multiple target molecules with the same label originated from the same cell. Multiple copies of the same target molecule with different labels originated from different cells. Multiple copies of the same target molecule with the same label originated from the same cell. The number of reads of the same sequence indicates the number of copies of the target molecule within a single cell. In certain embodiments, the efficiency of identification can be estimated, for instance using control target molecules. From this efficiency, the number of reads of the same sequence correlates to the number of copies of the target molecule within a single cell.

In certain embodiments, provided herein are methods for identifying one or more macromolecules in a plurality of cells. The methods comprise several steps. In one step, the one or more macromolecules are labeled in situ, for instance in cells. In a further step, the plurality of cells, comprising the labeled one or more macromolecules is pooled. In a further step, the one or more labeled macromolecules are separated from the pooled cells. In a further step, the labeled macromolecules are analyzed separately for identity and quantity. In certain embodiments, the labels are removed from the macromolecules. In certain embodiments, the macromolecules are identified. In certain embodiments, the labels are decoded. From the decoding, a macromolecule with a particular label code can be associated with the cell from which it originated, thereby identifying the macromolecule in the cell.

In certain embodiments, provided herein are methods for identifying and quantifying one or more macromolecules in a plurality of cells. The methods comprise several steps. In one step, the one or more macromolecules are labeled. In a further step, the plurality of cells, comprising the labeled one or more macromolecules is pooled. In a further step, the labeled macromolecules are analyzed separately for identity. In certain embodiments, the labels are removed from the macromolecules. In certain embodiments, the macromolecules are identified. In certain embodiments, the labels are decoded. Decoding can proceed with standard techniques. In certain embodiments, decoding is by oligonucleotide sequencing. From the decoding, each macromolecule with a particular label code can be associated with the cell from which it originated. In certain embodiments, the number of copies of an identified macromolecule with a particular label indicates the quantity of copies of that macromolecule in a single cell. In particular embodiments, the number of copies of an identified macromolecule with a particular label correlates to the quantity of copies of that macromolecule in a single cell.

The cells can be any cells without limitation. Useful cells include archae, prokaryote, and eukaryotes. In certain embodiments, the cells are bacterial cells. In certain embodiments, the cells are *E. coli* cells. In certain embodiments, the cells are yeast cells. In certain embodiments, the cells are *S. cerevisiae* cells. In certain embodiments, the cells are human cells. In certain embodiments, the cells are from a biological sample. In certain embodiments, the biological sample comprises a tissue sample, a cell sample, a cell extract sample, protein molecules, or combinations thereof.

In certain embodiments, each label is of the formula, or a stereoisomer or regioisomer thereof:

PRO-Ra'-L-Rb'-L-Rc'-Oligo $PEG_n$, wherein n is 5. In certain embodiments, at least one L is independently $PEG_n$, wherein n is greater than 5.

In certain embodiments, Rb' is of the formula, or a stereoisomer or regioisomer thereof:

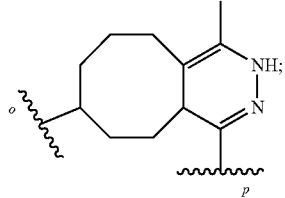 [SMILES: *C1=NNC(C)=C2CCCC(*)CCC12]

wherein o indicates a link to Oligo, and p indicate a link to PRO.

In certain embodiments, each label is of the formula, or a stereoisomer or regioisomer thereof:

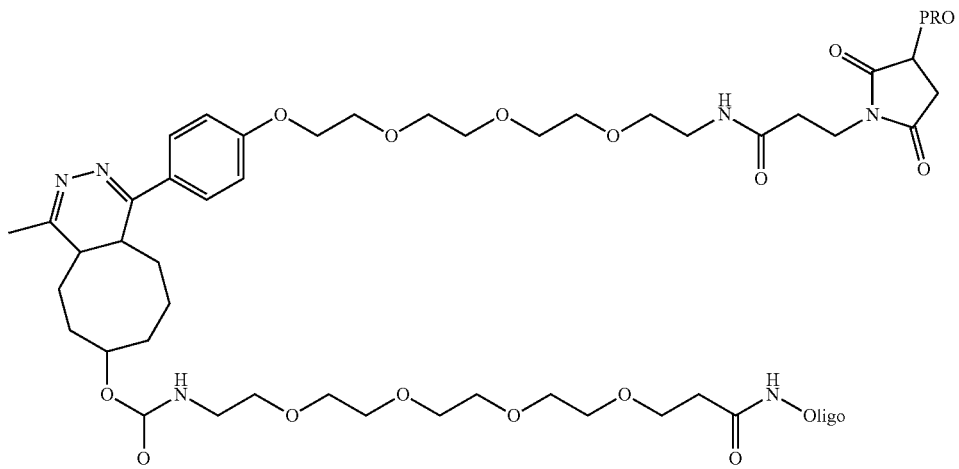

wherein PRO is a spycatcher protein and Oligo is an oligonucleotide.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

wherein
each Ra', Rb', and Rc' is independently a residue of one or more reactive groups;
each L is independently a linker;
PRO is a spycatcher protein;
and Oligo is an oligonucleotide.

The spycatcher protein is any spycatcher protein described herein or known to those of skill in the art. The oligonucleotide is an oligonucleotide as described herein. Each reactive group residue is a residue formed by reaction of a reactive group pair. The reactive group pair is any reactive group pair described herein. In certain embodiments, each reactive group residue is selected from triazoles, triazole derivatives, maleimide, maleimide derivatives, amides, and other reactive group residues known to those of skill in the art. Each linker is any divalent linker capable of linking the reactive groups in the formula.

In certain embodiments, each L is polyethylene glycol. In certain embodiments, each L is independently $PEG_n$, wherein n is an integer from 1 to 10. In certain embodiments, at least one L is independently $PEG_n$, wherein n is 1. In certain embodiments, at least one L is independently $PEG_n$, wherein n is 2. In certain embodiments, at least one L is independently $PEG_n$, wherein n is 3. In certain embodiments, at least one L is independently $PEG_n$, wherein n is 4. In certain embodiments, at least one L is independently

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

While technologies for measuring transcriptomes in single cells have matured, methods for measuring proteins and their modification states in single cells are still being actively developed. Unlike nucleic acids, proteins cannot be amplified, making detection of minute quantities from single cells difficult. The present example provides methods and compositions to quantify post-translational modification isoforms of a protein in single cells with high detection efficiency (~40%) using bulk separation methods.

In the methods, proteins from single cells are barcoded by tagging them with oligonucleotides. Cells are pooled together to increase total protein amounts to separate the isoforms by gel electrophoresis. Bands are excised from the gel, and the abundances of protein isoforms in single cells are quantified by sequencing the DNA barcodes from each band.

In these examples, this strategy of iDentification and qUantification sEparaTion (DUET) is used to measure histone protein H2B and its monoubiquitination isoform, H2Bub, in single yeast cells. The results revealed the heterogeneities of the ubiquitination levels of H2B in single cells from different cell-cycle stages, which have been obscured in ensemble measurements.

To accomplish this, proteins were tagged with DNA oligonucleotides, many cells were pooled together after each cell has been uniquely barcoded, the pooled lysate was separated with gel electrophoresis, and the barcodes from gel bands were quantified by bulk next-generation sequencing (NGS) (FIG. 1a). For the proof-of-concept experiment, a specific protein and its post-translational modification isoform were targeted.

Figure 1B:
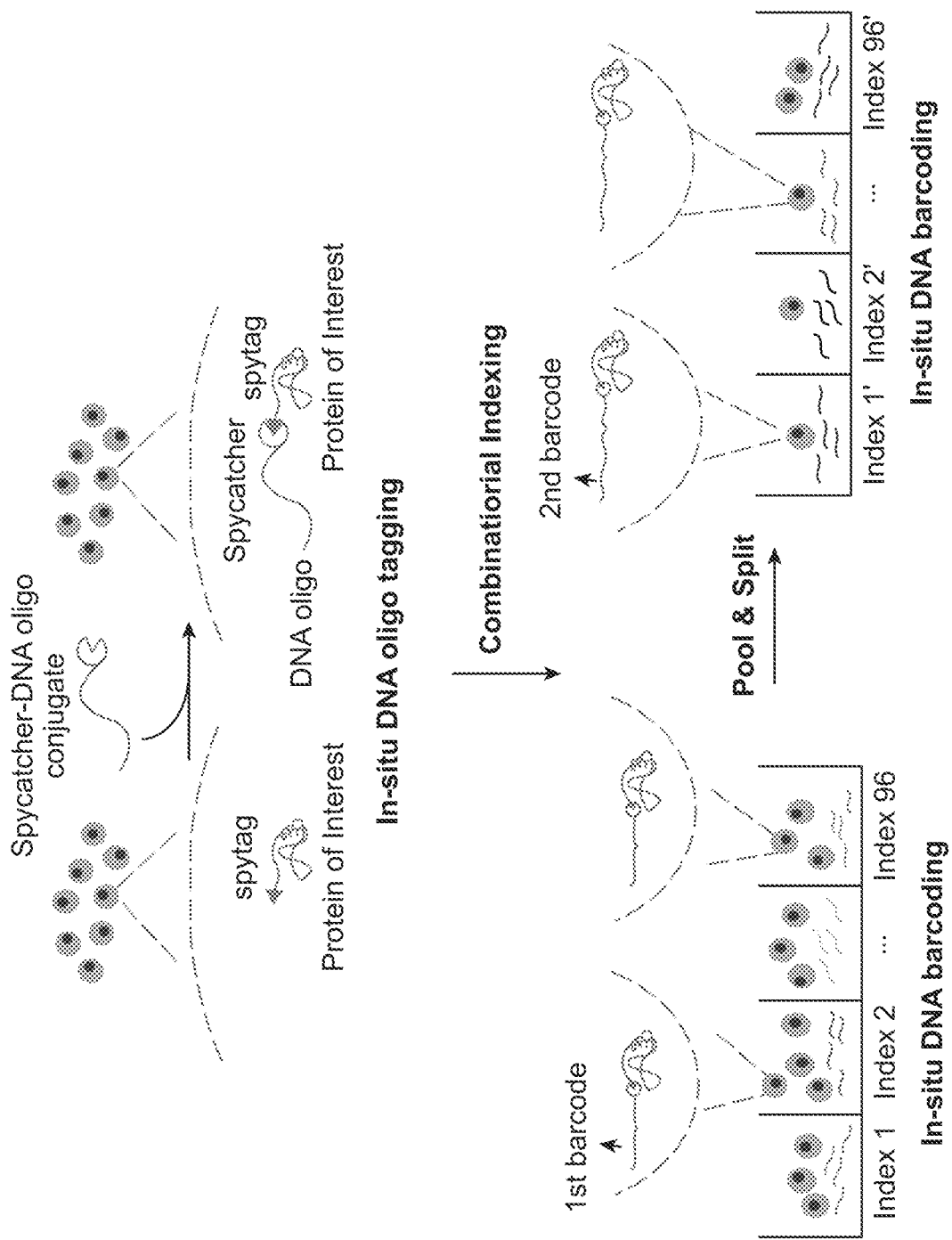
Figure 1C:
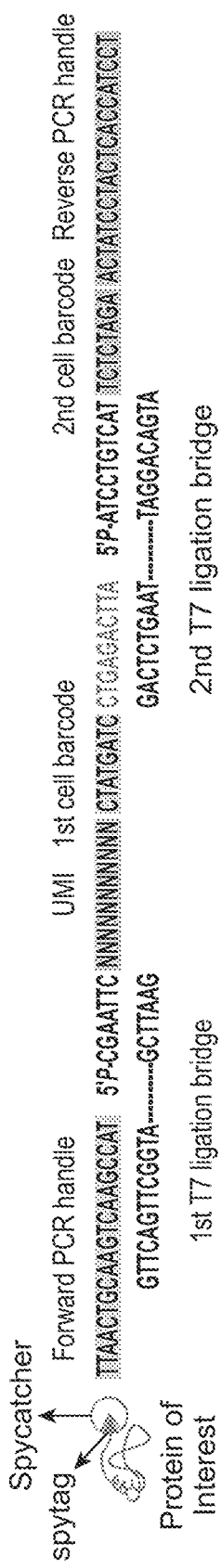
Figure 1D:
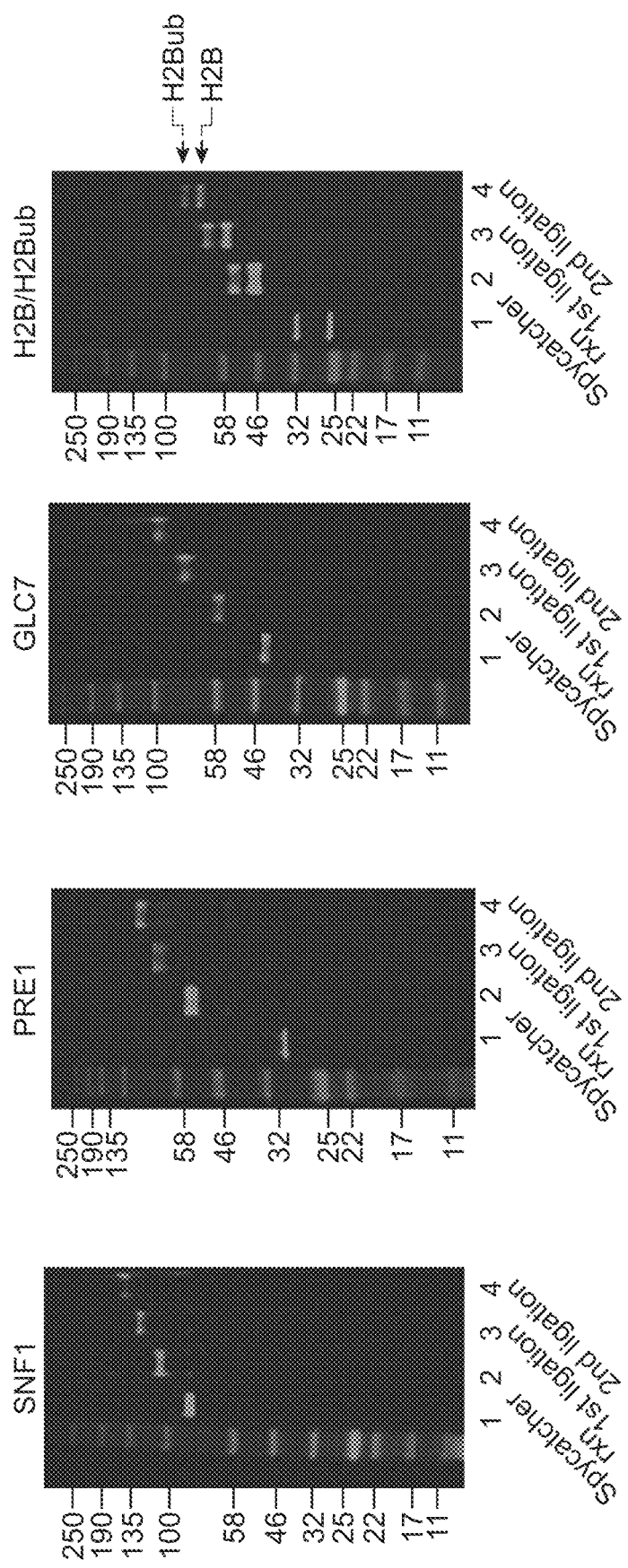
Figure 3A:
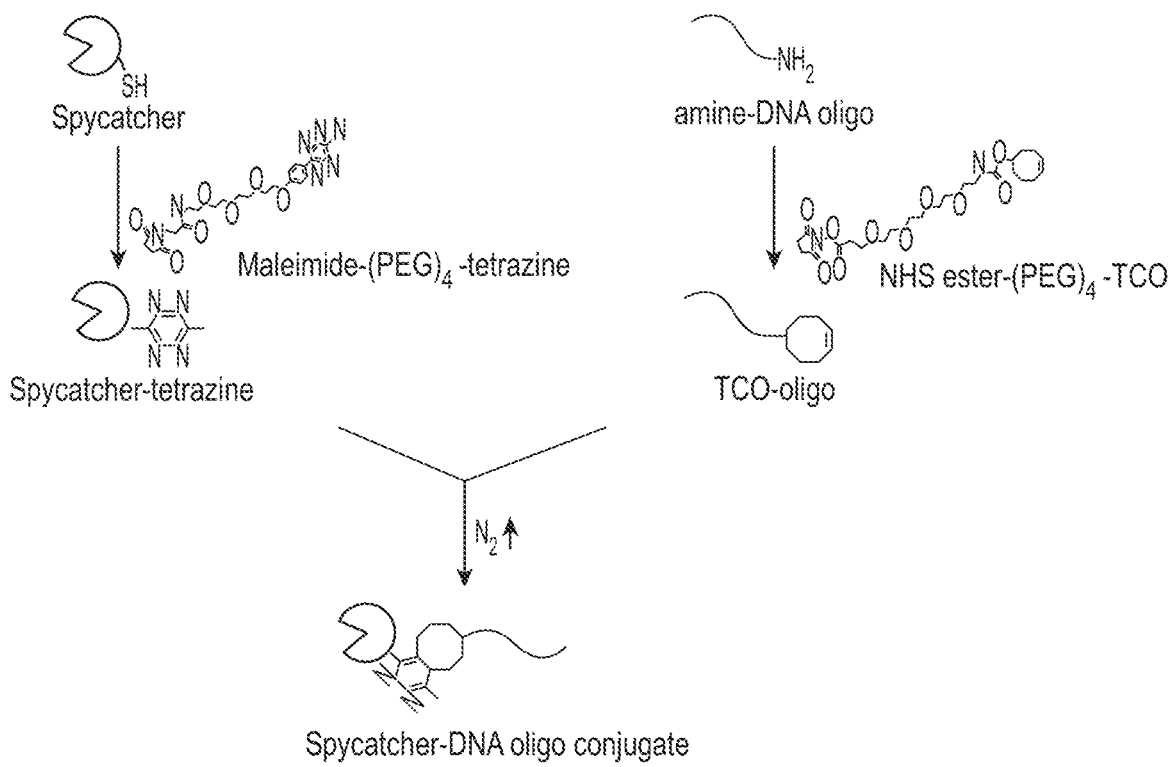
FIGS. 3a-3b. Spycatcher-DNA oligo conjugate.

First, a DNA oligo was tagged in situ to targeted proteins in fixed cells with a spytag/spycatcher system (FIG. 1b). Zakeri et al., 2012, *Proceedings of the National Academy of Sciences* 109, E690-E697. Spytag is a 13-amino-acid peptide that can form an isopeptide with its complementary 20 kd protein, Spycatcher, with high efficiency and specificity. Zakeri et al., 2012. To test the in-situ DNA oligo tagging, *S. cerevisiae* yeast strains were constructed containing spytag at the C-terminal of proteins of interest. 3×FLAG tag was also included together with spytag for Western blot analysis. A spycatcher-DNA oligo conjugate was synthesized using click-chemistry (FIG. 3a). The Western blot of whole-cell lysate using anti-FLAG antibody showed bands corresponding to the targeted protein shift up after reacting with spycatcher-DNA oligo conjugate, indicating successful conjugation of DNA oligos to the protein (FIG. 1d).

Several different target proteins were tested with different copy numbers and with different cellular localizations (High copy: H2B (nucleus) and PRE1 (cytoplasm); low copy: SNF1 and GLC7) (FIG. 1d). The in-situ tagging efficiency was above 90% for all the proteins tested (FIG. 4), demonstrating the general applicability of our strategy. Other tagging strategies such as unnatural amino acids can also be used in certain embodiments. Dieterich et al., 2006, *Proc. Natl. Acad. Sci. U.S.A.* 103; Chin, 2017, *Nature* 550, 53-60 (2017).

Figure 4A:
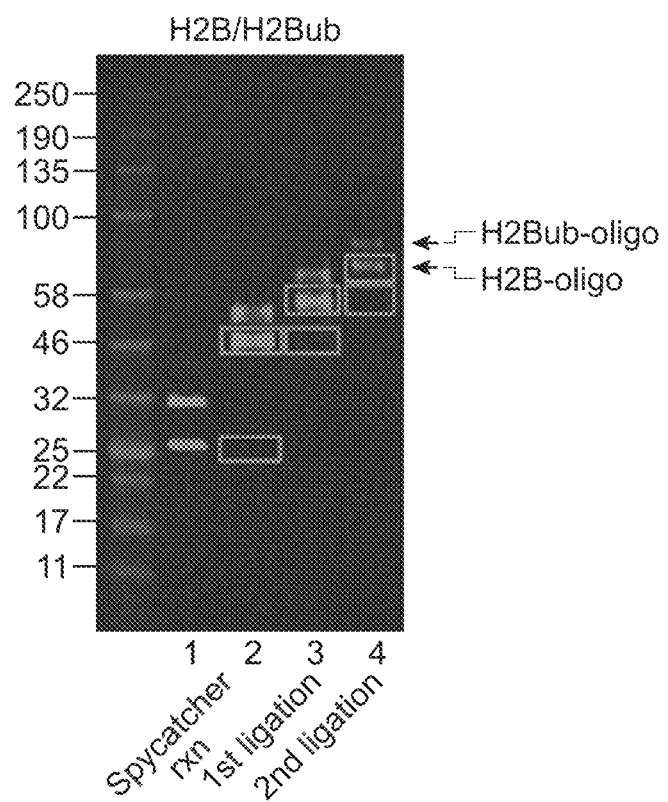
FIGS. 4a-4b. Western blot analysis of H2B after spycatcher reaction, the first ligation, and the second ligation.
Figure 4B:
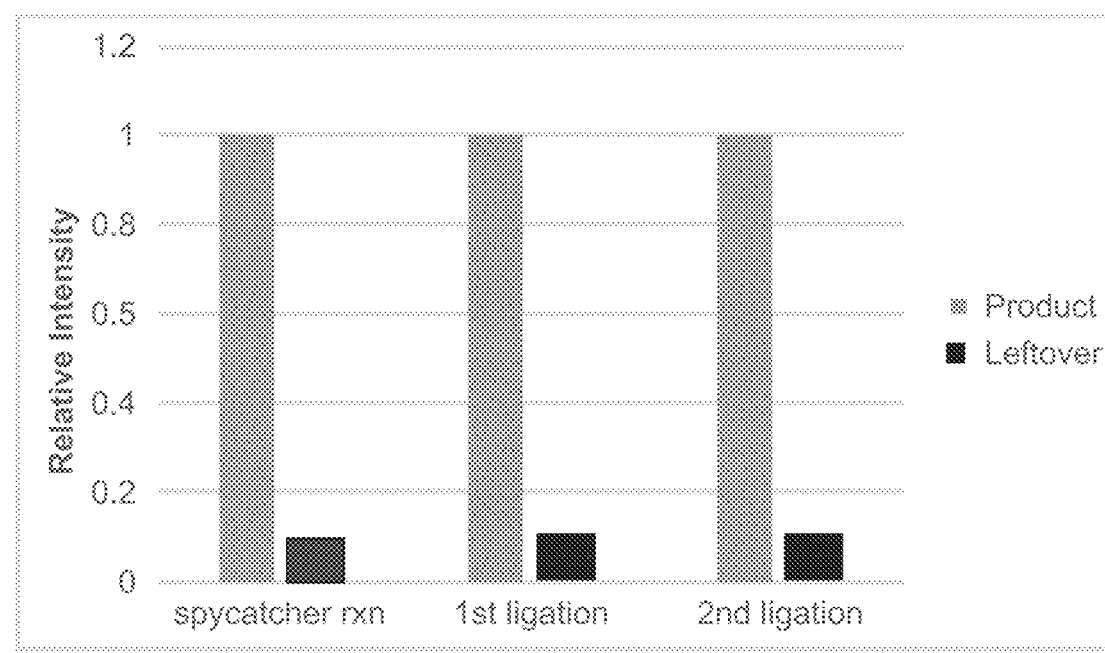

Second, we uniquely barcoded proteins in single cells by employing a combinatorial indexing scheme. Cusanovich, et al., 2015 *Science* 348, 910-914. Two sequential rounds of "pool-split" T7 ligation were performed to ligate barcode oligo to the proteins-spycatcher complexes inside the cells (FIG. 1b-c). Western blot showed that the bands corresponding to the targeted protein shift up sequentially after two rounds of ligation, indicating that the barcode oligo is successfully ligated (FIG. 1d). The T7 ligation efficiency was more than 90%, as estimated from band intensity (FIG. 4).

In each round of ligation, 96 oligos are used. With two rounds of barcoding, over 900 cells can be uniquely barcoded and aliquoted with low barcode collisions rate (<5%, Table).

| Cells Sampled | Expected Collision Rate |
| --- | --- |
| 1 | 0 |
| 10 | 0.001 |
| 100 | 0.005 |
| 900 | 0.048 |
| 1500 | 0.079 |
| 2000 | 0.104 |
| 5000 | 0.247 |

Figure 5:
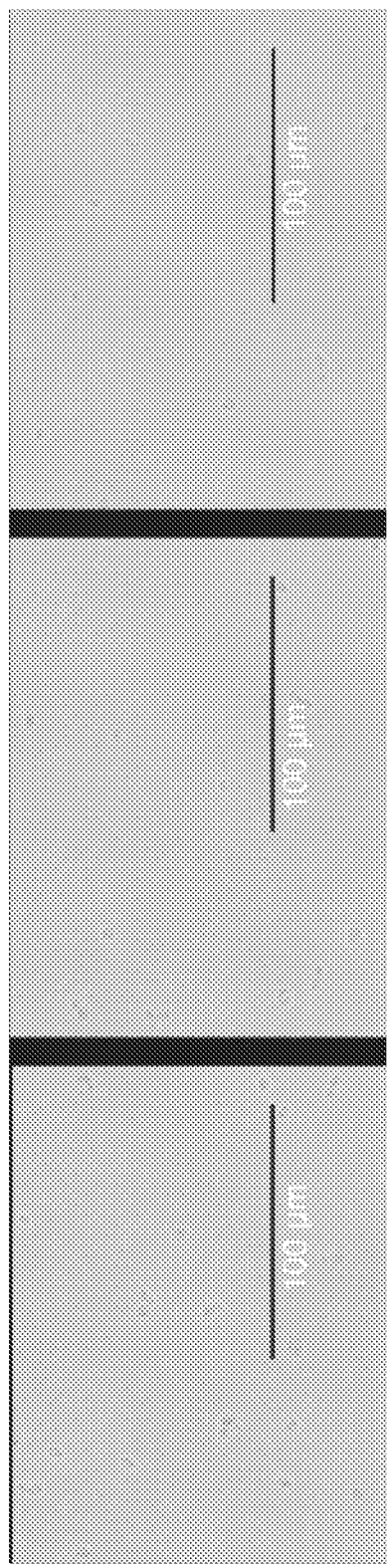
FIG. 5. Cell morphology under the microscope after spycatcher reaction, first ligation, and second ligation. Individual intact cells can be observed after each step without morphological changes, conforming that each single cell could be used as compartments during "split-pool" barcoding. (Scale bar: 100 um)

In addition to the cell barcodes, a 12nt random-base UMI sequence was incorporated in the first round of DNA barcode oligo (FIG. 1c), which can be used to provide accurate quantification of protein abundances in each cell and correct the amplification biases in NGS library generation. Kivioja et al., 2011, *Nat. Methods* 9, 72-74 (2011). Finally, cell morphology was well preserved after in-situ oligo tagging and two rounds of ligation (FIG. 5).

Figure 6A:
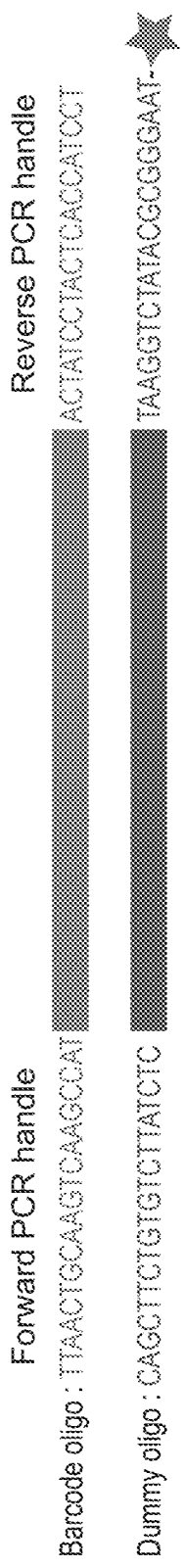
FIGS. 6a-6c. Design of dummy oligo.
Figure 6B:
Figure 6B:
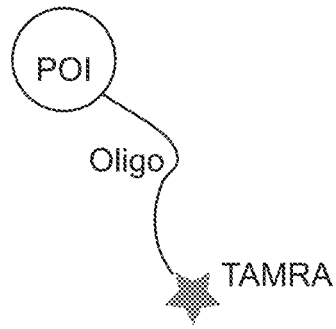

Third, the barcoded cells were pooled, lysed, and analyzed by gel electrophoresis. The targeted protein band was excised from the gel and the protein-oligo conjugate was extracted from the gel piece (FIG. 1a). Gel electrophoresis separates different protein isoforms, while their single-cell identities are preserved in the covalently attached oligo. For example, histone protein H2B and its monoubiquitination isoform H2Bub were separated by SDS-PAGE, as the monoubiquitinated H2Bub is 7 kD heavier and shows as an upper band in the gel (FIG. 1d). In the experiment, to boost the signal from the small number of barcoded cells (900 cells after second-round barcoding) and to avoid nonspecific sample loss during handling, around $10^{\wedge}6$ "dummy" cells were designed and prepared, in which the targeted proteins were tagged with oligos that are the same length as real barcode oligos, but with different sequences. As a result, the proteins from dummy cells would co-migrate with those from barcoded cells, but would not be amplified during PCR (FIG. 6). The dummy oligo also had a TAMRA dye at 3' end for band visualization on the gel (FIG. 6b). To achieve high-efficiency gel recovery, dissolvable polyacrylamide gel was used. Takemori et al., 2017, *Anal. Chem.* acs.analchem.7b00357 (2017).

Figure 2A:
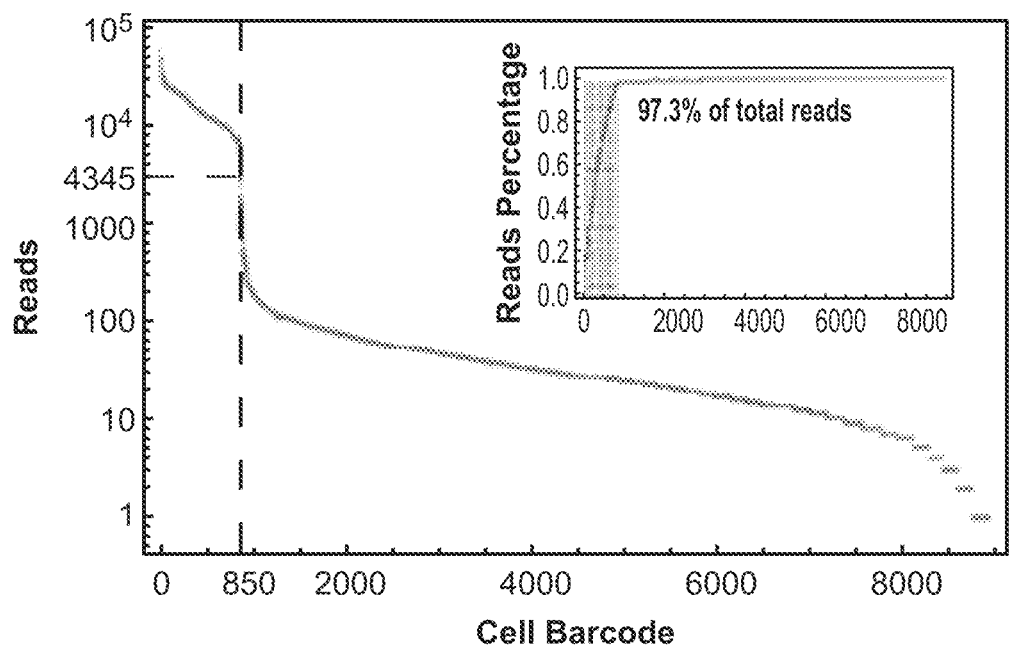
FIGS. 2a-2g. Quantification of H2B and its mono-ubiquitination H2Bub abundances in single yeast cells.

Finally, the protein copy numbers were quantified in single cells by analyzing the UMIs in the sequencing reads. The real cell barcodes were identified by plotting the total number of reads per barcode in descending order (FIG. 2a). A clear cutoff could be identified to separate real cell barcodes with a high number of UMI reads from spurious cell barcodes with a low number of reads, which are likely from PCR and sequencing errors. 850 real cell barcodes were identified, which agreed with experimental design (~900 cells are aliquoted). The same set of cell barcodes were also identified from the H2Bub sample (848 out of 850 H2B cell barcodes) (FIG. 7), further confirming that those barcodes represent real cells. To quantify the protein copy numbers in single cells, the UMIs associated with each cell barcode were counted. The length of UMI (12nt) had enough coding space to encode the proteins in single cells (FIG. 8a-b) and that sequencing depth was sufficient enough to sample all the possible UMIs (FIG. 6c), such that the copy number of proteins were accurately quantitated by the UMIs. Ogawa et al., 2017, *Sci. Rep.* 7, 1-7 (2017). On average, 4065±1798 UMI of H2B proteins per cell were detected using 10% of the extracted materials. There are estimated 101430±63961 copies of H2B per cell. Breker et al., 2013, *J. Cell Biol.* 200, 839-850 (2013). From this, detection efficiency was estimated to be 40±18%, with most of the loss from handling and gel electrophoresis. Alternative methods of separation can be explored such as 2D gels and high dimensional liquid chromatography, in certain embodiments. Washburn et al., 2001, *Nat. Biotechnol.* 19, 242-247 (2001).

Figure 2B:
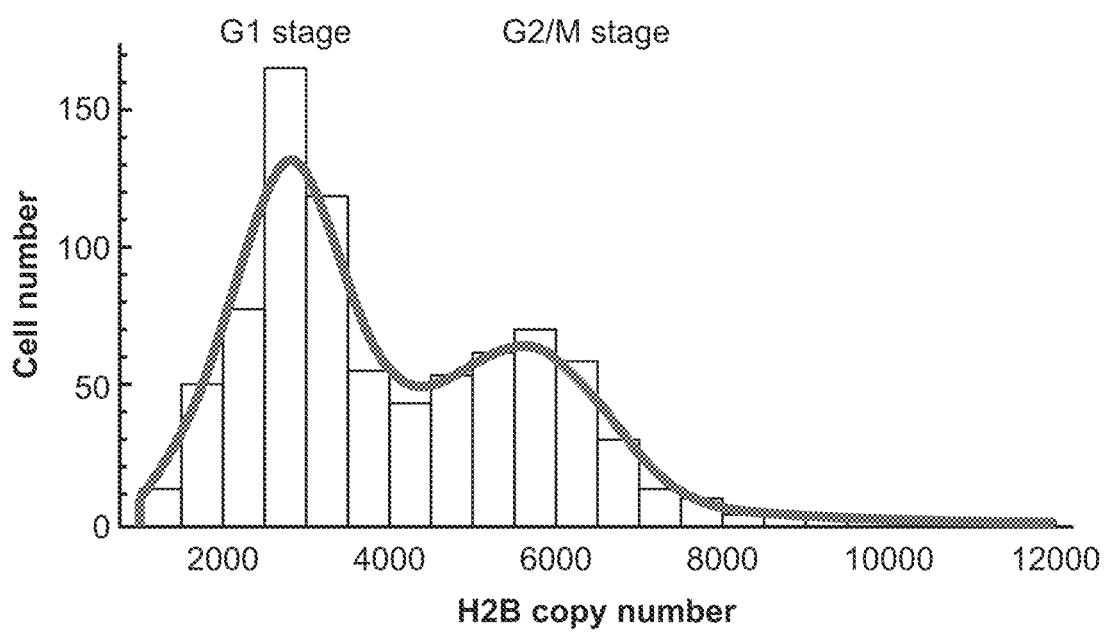
Figure 2C:
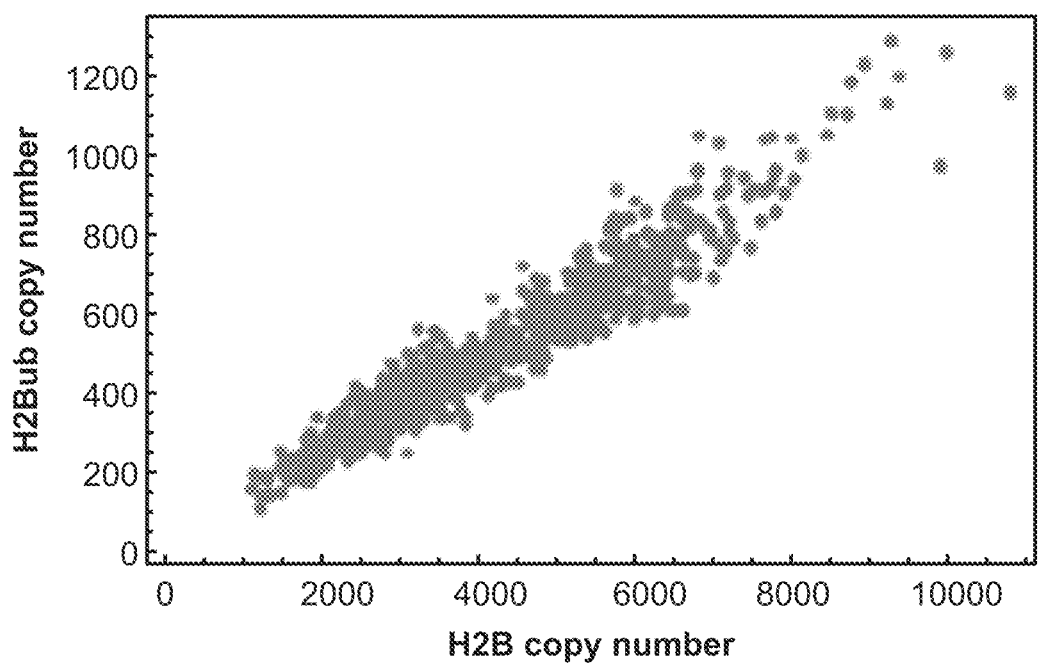
Figure 2D:
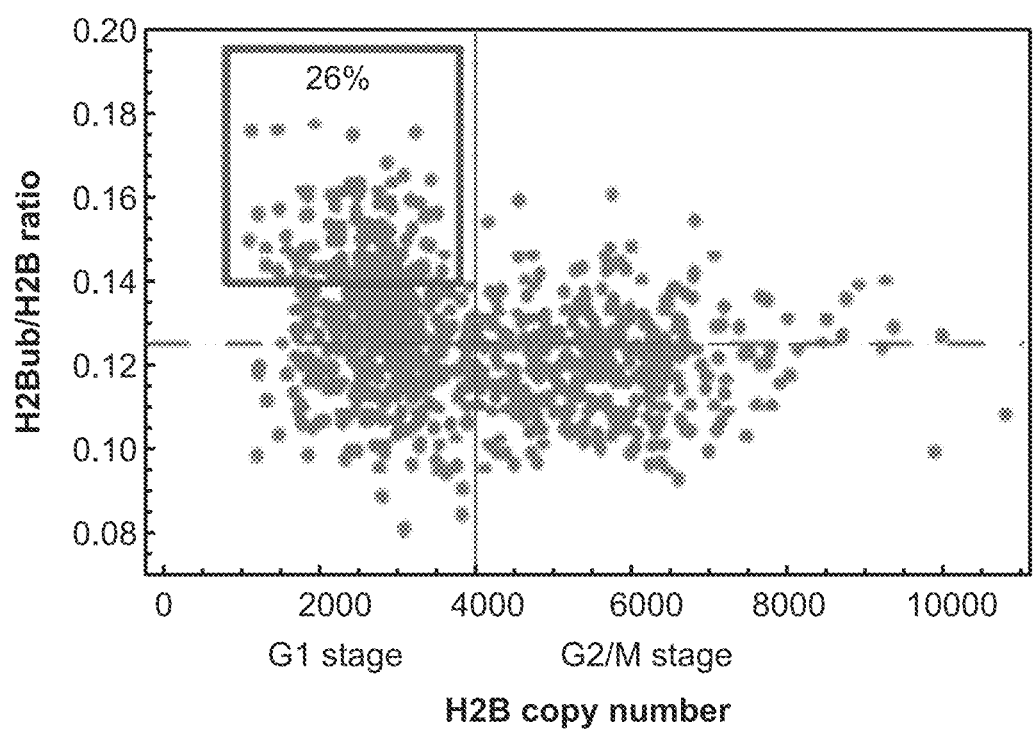
Figure 2E:
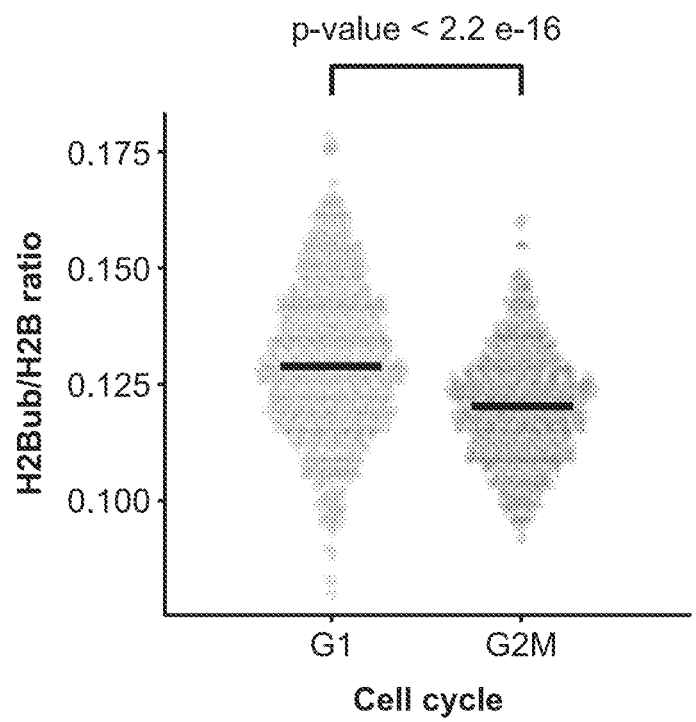

Heterogeneity in the copy numbers of H2B and its monoubiquitination isoform of H2B (H2Bub) were quantified in single cells (FIG. 2b-c). H2B expression is tightly coupled with DNA replication. Garmendia-Torrese et al., 2018 *Elife* 7; Eriksson et al., 2012, *Genetics* 191, 7-20 (2012). The histogram of the H2B copy number determined from the method showed a bimodal distribution, which corresponds to different cell-cycle stages (G1 v. s. G2/M). And the copy numbers of the cells at G2/M stage were roughly two-fold of the cells at G1 stage. This result indicated that the method accurately quantified the relative level of H2B in single cells (FIG. 2b). The ratio between H2Bub to H2B in single cells was calculated (FIG. 2d). Interestingly, cells at different cell-cycle stages (as indicated by the H2B copy number) showed different H2Bub/H2B ratio distributions (FIG. 2d-e). Specifically, 26% of cells at G1 stages had high ratio of H2Bub to H2B (>0.14), compared with only 5% of cells at G2/M stages.

Figure 2F:
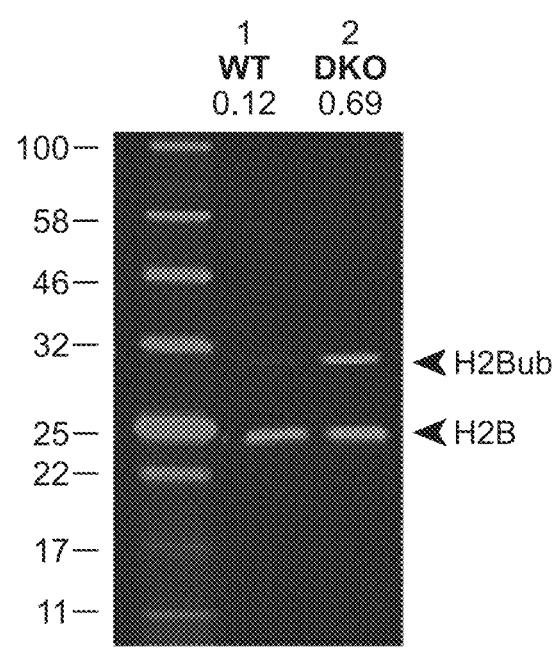
Figure 2G:
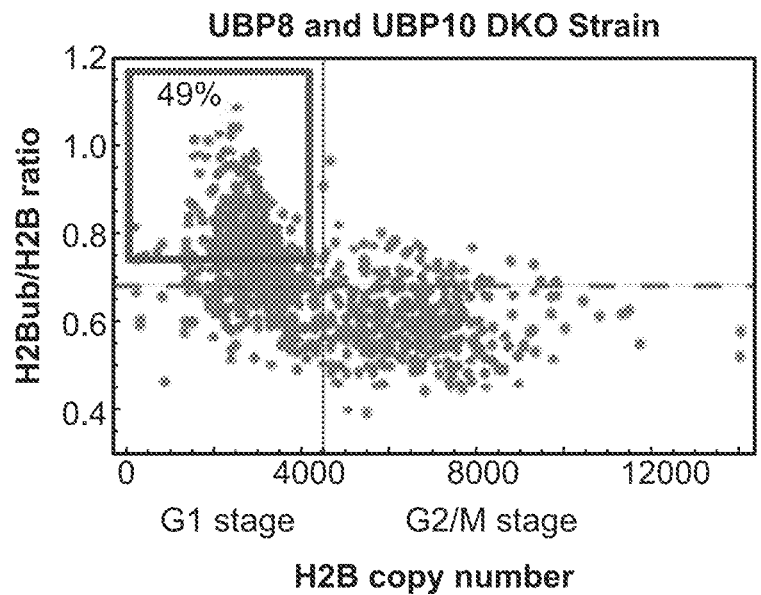

To further investigate this, the method was applied on a double-knockout yeast strain in which two de-ubiquitination enzymes (UBP8 and UBP10) that remove ubiquitin from H2B are deleted. Schulze et al., 2011, *Genes Dev.* 25, 2242-2247. As expected, the H2Bub level was elevated in this strain (H2Bub/H2B ratio: 0.69), as estimated from ensemble Western blot (FIG. 2f). However, 49% of cells at G1 stages still had high ratio of H2Bub to H2B (>0.74), compared with 5% of cells at G2/M stage (FIG. 2g). These results suggest that while UBP8 and UBP10 sets the baseline levels of ubiquitination of H2B, a different mechanism might control the dynamics of H2Bub during the cell cycle.

This Example demonstrates that by separating the identification and the quantification steps, high detection efficiency (~40%) and isoform resolution was achieved in single cells. This approach of iDentification and qUantification sEparaTion (DUET) required no single cell handling and using only bulk biochemistry and sequencing in liquid phase to enable robust analysis of non-amplifiable species from single cells. This approach could be extended to detect other post-translational modification isoforms, such as phosphorylation, provided different isoforms could be sufficiently resolved. Kinoshita et al., 2009, *Nat. Protoc.* 4, 1513-1521. This approach could also potentially generalize to the proteome level with the incorporation of unnatural amino acids to label all translated proteins that can be clicked to oligonucleotide and separated by high dimensional gels or liquid chromatography followed by protein identification with mass spectrometry and single-cell quantification with NGS. Dieterich et al., 2006, *Proc. Natl. Acad. Sci. U.S.A.* 103; Rabilloud & Lelong, 2011, *J. Proteomics* 74, 1829-1841; Washburn et al., 2001, *Nat. Biotechnol.* 19, 242-247 (2001).

Example 2—Methods

Yeast Strains and Plasmids

The *S. cerevisiae* strains used in this study were BY4741 (MATa his3 leu2 met15 ura3). The standard cloning procedure was performed[1] to tag the C-terminal of target protein with spytag and 3×FLAG.

Cell Culture and Fixation

Fresh colonies of yeast strain were grown in YPD until OD600 of ~0.5 (1.0 ml culture). Cells were then fixed by 1% formaldehyde (Thermo Scientific, 28908) at 30° C. for 30 mins with gentle shaking. Cells were then harvested and washed by buffer B (1.2M sorbitol/0.1M sodium phosphate, pH 7.4) three times. The cells were spheroplasted using 100 µg (Zymo Research, E1006) and 10-µL fresh beta-mercaptoethanol in 1 mL of buffer B cell suspension for 1.0 min at 37° C. with gentle shaking. After the spheroplasting reaction, the cells were gently washed with buffer B three times. Cells were post-fixed in 1% formaldehyde in 1×PBS/0.6M KCl for 30 min at RT. Cells were washed with buffer B three times again after post-fixation.

Spycatcher-DNA Oligo Conjugate Synthesis

Figure 3B:
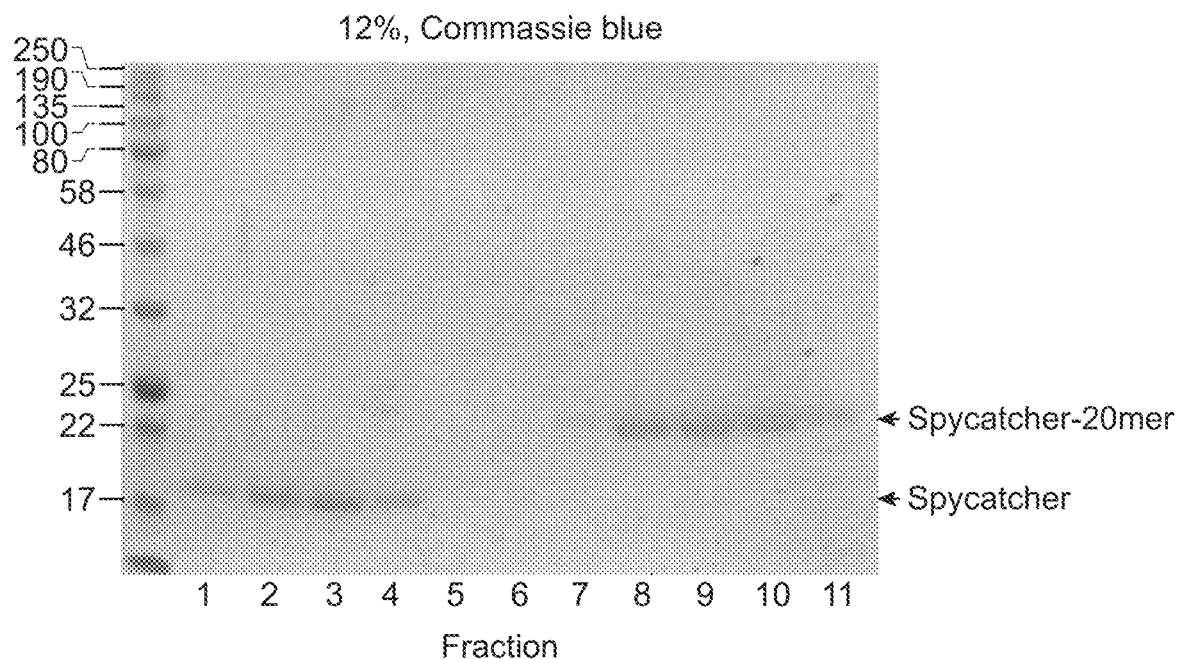

The strategy for synthesizing spycatcher-DNA oligo conjugate is shown in FIG. 3. Spycatcher with 6×His-tag and a cysteine sequence at C-terminal was purified using standard purification method. To prepare spycatcher-tetrazine, spycatcher was firstly reduced by TECP (Thermo Scientific 77720) to remove the potential intermolecular disulfide bond. Excess TCEP was then removed by PD-10 column (GE Healthcare). The spycatcher was reacted with maleimide-PEG$_4$-tetrazine (Click Chemistry Tools, 1068-10) via the thiol group in cysteine, and the reaction product (spycatcher-tetrazine) was separated from unreacted maleimide-PEG4-tetrazine by PD-10 column. To prepare TCO-oligo, 5'-amine-modified oligonucleotide (IDT) was reacted with TCO-peg4-NHS ester (Click Chemistry Tools, A137-2), and the reaction mixture was purified by HPLC. Finally, to prepare spycatcher-DNA oligo conjugate, spycatcher-tetrazine was reacted with an equal molar amount of TCO-oligo via the click chemistry between tetrazine and TCO (FIG. 3a). Spycatcher-oligo conjugate was purified from unreacted spycatcher and TCO-oligo by ion-exchange chromatography (FIG. 3b) and stored with 50% glycerol in PBS at −20° C. until further usage.

In-Situ DNA Oligo Tagging

10 µM spycatcher-DNA oligo conjugate was reacted with cells in 1×PBS/0.6M KCl solution containing protease inhibitor cocktail (Sigma SRE0055). The reaction was incubated 2 hrs at RT with gentle shaking. After the spycatcher-oligo reaction, cells were washed with buffer B three times.

Pool-Split Combinatorial Barcoding with T7 Ligation

Cells after in-situ DNA tagging were distributed into a 96-well plate. T7 ligation reaction buffer containing T7 ligase (NEB M0318 S), 1st round ligation adapter (5 µM) and 1st round barcoding oligos (5 µM) were added into each well. The plate was incubated for 2 hr at room temperature with gentle shaking. After 1st round barcode ligation, cells were pooled together, washed with bufferB three times, and distributed into another 96-well plate. T7 ligation reaction buffer containing T7 ligase, 2nd round ligation adapter (5 µM) and 2nd round barcoding oligos (5 µM) were added into each well. The plate was incubated for 2 hr at room temperature with gentle shaking. After 2nd round barcode ligation, cells were pooled together and washed with buffer B three times. The cell morphology was checked under the microscope after spycatcher-oligo conjugation, 1st ligation, and 2nd ligation to make sure the cells remain intact during this procedure (FIG. 5). The cell density was measured using a hemocytometer and a cell-suspension solution containing 900 cells was aliquoted using flow cytometry.

Figure 6C:
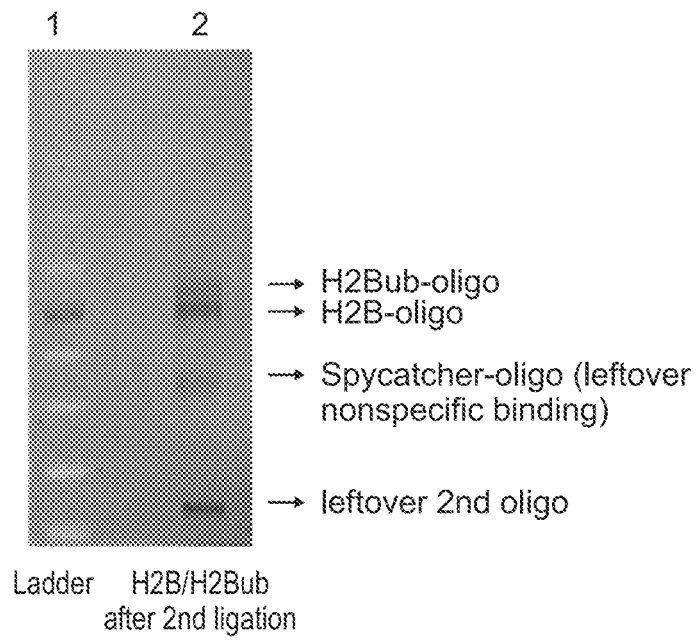

For "dummy" sample preparation, spycatcher-DNA oligo conjugate was synthesized with the dummy sequence using the same method as described previously. Then cells were reacted with the spycatcher-dummy oligo, sequentially ligated with 1st round barcode oligos and 2nd round barcode oligos using the same methods as before, but without pool-splitting. The dummy sample has different sequence in the PCR handle parts so that it will not be amplified by primers for Illumina sequencing library preparation (FIG. 6a). In addition, the 3' end of 2nd-ligation oligo is modified with a rhodamine dye TAMRA, to enable visualization of the ligation bands in gel analysis by a typhoon scanner (FIG. 6b-c). The dummy sample was mixed with the aliquot of real barcoded sample (~900 cells) for further analysis.

Gel Electrophoresis and Protein DNA Complex Recovery

2×laemmli buffer (Bio-Rad, 1610737) was added to the cells (containing both dummy cells and barcoded cells) and boiled at 95° C. for 10 min. The sample was then loaded in a 10% dissolvable polyacrylamide gel. The dissolvable PAGE was made with a labile crosslinker, ethylene-glycol-diacrylate (EDA) (Sigma 41608), which allows for high recovery yield from the gel[2]. The target protein-oligo conjugate bands were visualized using a Typhoon scanner to image with TAMRA fluorescence. The bands are cut off from the gel, and the protein-oligo complex were recovered. A blank gel piece was also cut and extracted (FIG. 7a) to estimate the background introduced during gel electrophoresis.

Library Preparation and Sequencing

Two rounds of PCR amplification were carried out for next-generation sequencing library preparation. 10% of the materials recovered from the gel was used for PCR amplification. First, the DNA part of the protein-DNA complex was amplified via its PCR handle. Then in second-round PCR, sequencing adapters were appended using NEBNext Multiplex Oligos for Illumina (NEB). The amplification conditions for the first round PCR were as follows: 95° C. 1 min, then 10-15 cycles at 95° C., 10 s/62° C., 15 s/65° C. 30 s, and a final extension at 65° C. 3 min. The number of cycles required for the first-round PCR was determined by analyzing a small aliquot of the sample on a qPCR machine. The number of cycles was determined as the start point of exponential phase amplification. The PCR amplification condition for the second-round PCR was as follows: 95° C. 1 min, then 4 cycles at 95° C. 10 s, 62° C. 15 s, 65° C. 30 s, and a final extension at 65° C. 3 min. After each round of PCR, PCR amplicons were run on 3% agarose gel and purified using gel extraction kit (Thermo Scientific, K210012). The PCR-amplified library was quantified using a Qubit High-sensitivity DNA kit (Invitrogen). The final purified amplicons were sequenced on a HiSeq 2500 (Illumina) with the targeted read depth of 5-25 million per gel band.

Data Analysis

To estimate the "collision" rate (the number of barcodes representing more than two cells), the sampling process was simulated (Table 1) using the procedure described in the previous work[3]. With 9,216 possible barcode combinations, the sampling of 900 cells should result in an expected collision rate lower than 5%. Therefore 900 cells were aliquoted in the experiment for the following analysis.

Figure 7A:
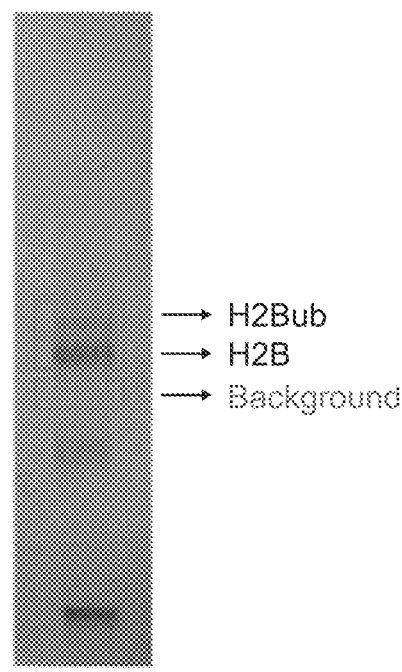
FIGS. 7a-7d. Identification of cell barcodes.
Figure 7B:
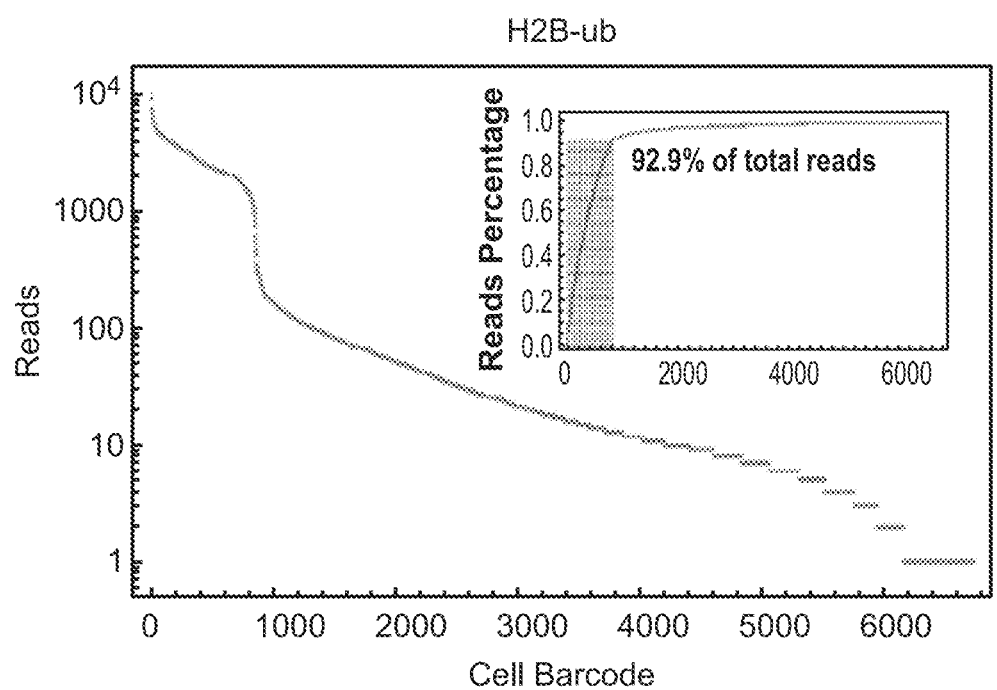
Figure 7C:
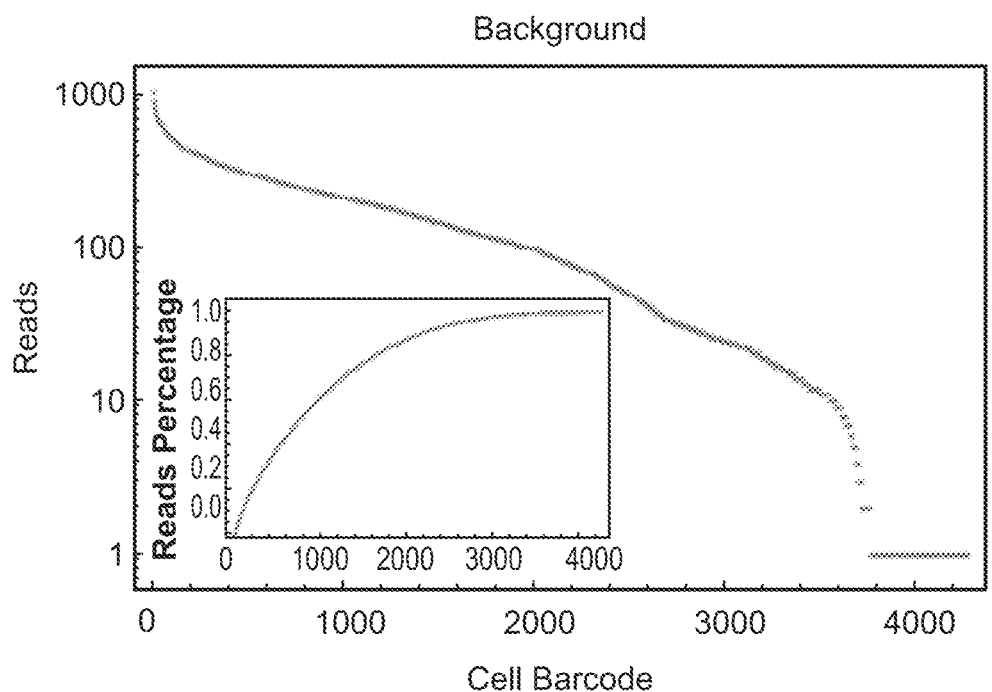
Figure 7D:
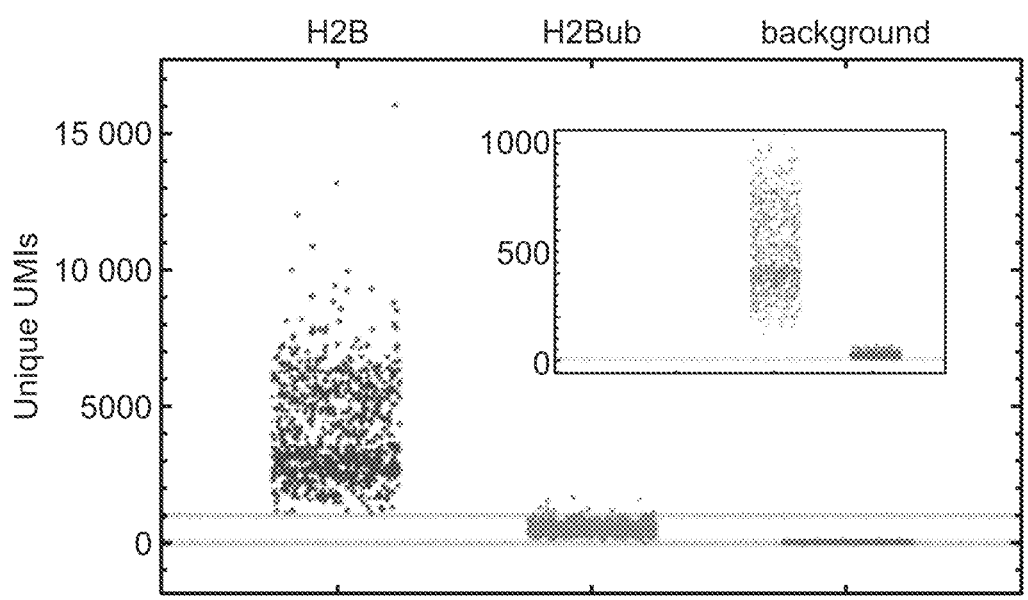

The sequencing reads were first filtered based on the constant fixed region in the oligo (the constant region includes the PCR handle, the first T7 ligation site, and second T7 ligation site). Reads that had more than one mismatch against the constant region were disregarded. Then, the 1st round cell barcode and 2nd round cell barcode were connected together to generate the full cell barcode. Reads with cell barcodes which did not match the set of barcode combinations (9216 in total) were disregarded. The number of reads for each barcode was then calculated and the real-cell barcodes were identified from spurious cell barcodes as the former have a much higher number of reads than the latter (FIG. 7b). While the real barcodes could be identified from both H2B sample and H2Bub sample, they can't be identified from the background sample (FIG. 7c). In addition, the number of unique UMIs is significantly lower in the background band compared with the targeted protein band, indicating the gel background is low.

Figure 8A:
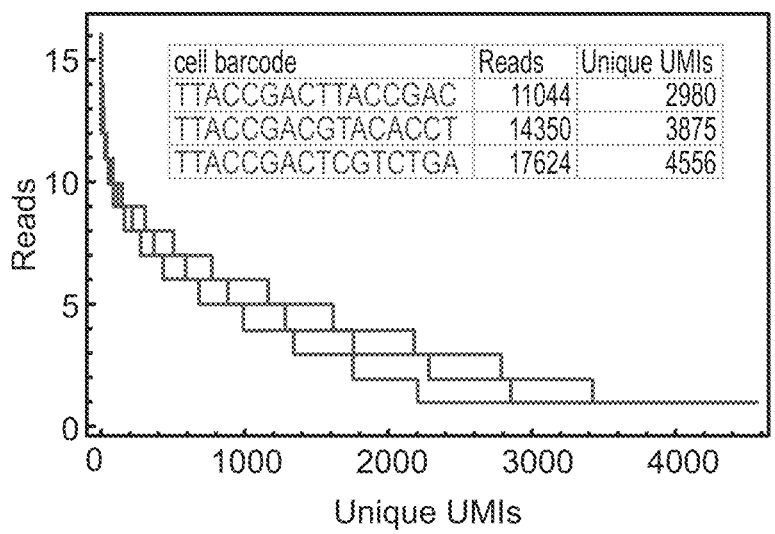
FIGS. 8a-8c. Quantification of protein copy numbers by counting UMIs.
Figure 8B:
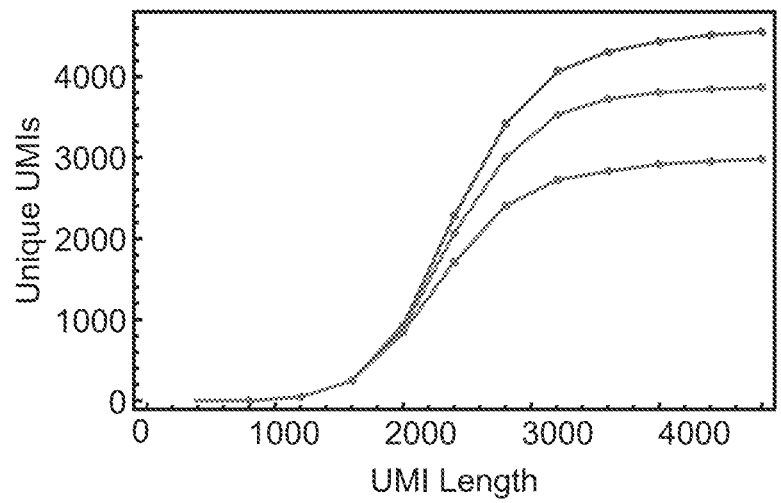
Figure 8C:
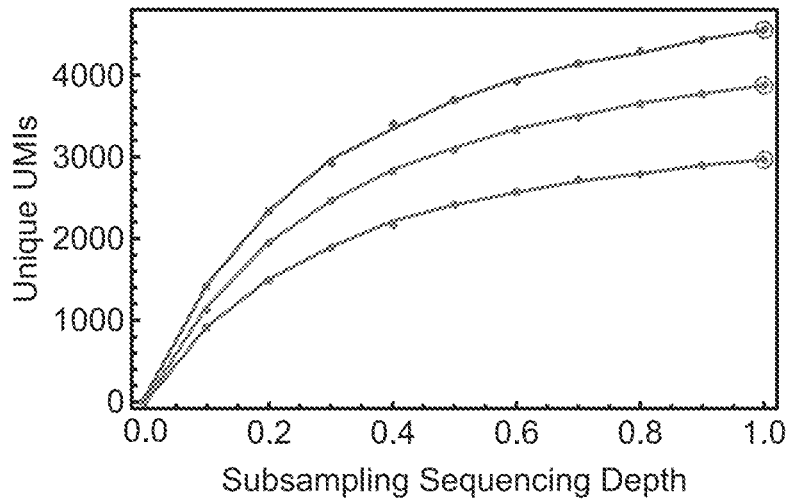

To verify that the UMIs had enough coding space to encode all the proteins in single cells, we counted how many unique UMIs we could identify from sequencing results when we computationally shortened the UMIs (FIG. 8a-b). The number of UMIs increased with the length of the UMIs and reached a plateau after around 10nt, indicating that the length of UMI (12nt) have enough coding space to encode all proteins in single cells. To verify that the sequencing depth was high enough to sample all the UMIs, we computationally subsampled the sequencing reads and calculated how many UMIs observed were associated with single-cell barcodes (FIG. 8c). As sequencing depth increased, the number of uniquely identified UMIs increases and reached a plateau at full sequencing depth (1.0), indicating that all the UMIs are sufficiently sampled. Different sequencing depths were needed for different proteins to saturate the UMIs. For example, for the H2B sample, 25 million reads were needed, while for the H2Bub sample, only 5 million reads were required for library saturation. This reflects the different complexity of these two libraries, which agrees with the different copy numbers of these two proteins inside the cells. UMI error correction methods, such as UMI-tools, could be used to increase the quantification accuracy in certain embodiments. Levine et al., 2013, *Science* 342, 1193-1200 (2013).

All publications and patent, applications cited in this specification are herein incorporated by reference as if each individual publication or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof. Accordingly, it is intended that the scope of the subject matter limited solely by the scope of the following claims, including equivalents thereof.

The invention claimed is:

1. A method for identifying one or more macromolecules in a plurality of cells with single cell resolution, wherein each macromolecule is a nucleic acid, protein, sugar, or lipid, and wherein each macromolecule comprises a tag, the method comprising the steps of:
   a. labelling, in the plurality of cells, the one or more macromolecules with one or more labels to form one or more labelled macromolecules, wherein each label comprises an oligonucleotide covalently linked to at least one moiety, and Wherein the at least one moiety is covalently or non-covalently linked to the tag on each of the one or more labelled macromolecules;
   b. pooling the plurality of cells;
   c. lysing the pooled plurality of cells;
   d. separating each of the one or more labelled macromolecules from the lysed plurality of cells; and
   e. for each of the one or more labelled macromolecules, separately:
      i. identifying each macromolecule;
      ii. decoding the label of each macromolecule, thereby identifying the cell that comprised the labelled macromolecule.

2. A method for quantifying one or more macromolecules in a plurality of cells with single cell resolution, wherein each macromolecule is a nucleic acid, protein, sugar, or lipid, and wherein each macromolecule comprises a tag, the method comprising the steps of:
   a. labelling, in the plurality of cells, the one or more macromolecules with one or more labels to form one or more labelled macromolecules, wherein each label comprises an oligonucleotide covalently linked to at least one moiety, wherein the at least one moiety is covalently or non-covalently linked to the tag on each of the one or more labelled macromolecules;
   b. pooling the plurality of cells;
   c. lysing the pooled plurality of cells;
   d. separating each of the one or more labelled macromolecules from the lysed plurality of cells;
   e. for each of the one or more labelled macromolecules, separately:
      i. identifying each macromolecule; and
      ii. quantifying the number of labels of each macromolecule, thereby quantifying the amount of the labelled macromolecule per cell.

3. The method of claim 1, wherein the labelling is by combinatorial ligation.

4. The method of claim 1, further comprising cleaving each label from the one or more labelled macromolecules prior to identifying.

5. The method of claim 1, wherein each macromolecule is a protein.

6. The method of claim 1, wherein the oligonucleotide comprises one or more barcode sequences.

7. The method of claim 1, wherein each macromolecule is a protein, comprising a tag, optionally wherein said tag is selected from FLAG, polyhistidine, a spytag, a non-natural amino acid, or a small molecule bound to the protein covalently or non-covalently.

8. The method of claim 1, wherein each macromolecule is a protein comprising a non-natural amino acid.

9. The method of claim 8, wherein the non-natural amino acid is selected from the group consisting of modified cysteine, modified lysine, a modified amino terminal amino acid, modified glutamine, azidohomoalanine, and homopropargylglycine.

10. The methods of claim 1, wherein the tag is a small molecule.

11. The method of claim 10, wherein the tag is an inhibitor of one of the one or more macromolecules.

12. The method of claim 7, wherein the tag is a spytag.

13. The method of claim 1, wherein each macromolecule is a protein, the tag is a spytag, and the at least one moiety comprises a spycatcher.

14. The method of claim 1, wherein each macromolecule is a protein wherein the tai is a spytag, and wherein the at least one moiety comprises a spycatcher.

15. The method of claim 1, wherein each macromolecule is a protein, wherein the tag is a spytag, wherein the at least one moiety comprises a spycatcher, and wherein the oligonucleotide comprises one or more barcode sequences.

16. The method of claim 1, wherein the at least one moiety is linked to the tag via an amide bond, a click residue, a tetrazole, a tetrazole derivative, an antibody-antigen pair, an avidin-biotin pair, or a spytag-spycatcher pair.

17. The method of claim 1,
wherein the oligonucleotide comprises two polymerase chain reaction handles, one or more unique molecular identifiers (UMIs) between the polymerase chain reaction (PCR) primer handles, and one or more barcode sequences that can be combinatorial synthesized and ligated to barcode individual cells between the (PCR) primer handles.

18. The method of claim 1, wherein the oligonucleotide is identified by sequencing.

19. The method of claim 1,
wherein the macromolecule is identified by electrophoresis, chromatography, or spectrometry,
wherein said electrophoresis is gel electrophoresis, phosphorylation sensitive gel electrophoresis, or two-dimensional gel electrophoresis,
wherein said chromatography is liquid chromatography or high performance liquid chromatography, and
wherein said spectrometry is mass spectrometry, time of flight mass spectrometry, or matrix-assisted laser desorption/ionization mass spectrometry.

20. The method of claim 1, wherein each oligonucleotide is decoded by sequencing.

* * * * *